United States Patent [19]

McAdon et al.

[11] Patent Number: 5,965,756
[45] Date of Patent: Oct. 12, 1999

[54] FUSED RING SUBSTITUTED INDENYL METAL COMPLEXES AND POLYMERIZATION PROCESS

[75] Inventors: Mark H. McAdon; Jasson T. Patton; Peter N. Nickias; Ravi B. Shankar; Francis J. Timmers, all of Midland, Mich.; Brian W. Kolthammer, Lake Jackson, Tex.; Daniel D. VanderLende, Sugar Land, Tex.; Steven M. Ueligger, Angleton, Tex.

[73] Assignee: The Dow Chemical Company, Midland, Mich.

[21] Appl. No.: 08/949,505

[22] Filed: Oct. 14, 1997

Related U.S. Application Data

[60] Provisional application No. 60/034,817, Dec. 19, 1996.

[51] Int. Cl.$^6$ .................... C07F 17/00; C07F 7/28
[52] U.S. Cl. .................... 556/11; 556/12; 556/19; 556/21; 556/22; 556/52; 502/103; 502/117; 502/152; 526/126; 526/160; 526/943
[58] Field of Search .................... 556/11, 12, 19, 556/21, 22, 52; 502/103, 117, 152; 526/126, 160, 943

[56] References Cited

U.S. PATENT DOCUMENTS

| 5,055,438 | 10/1991 | Canich | 502/117 |
|---|---|---|---|
| 5,057,475 | 10/1991 | Canich et al. | 502/104 |
| 5,064,802 | 11/1991 | Stevens et al. | 502/155 |
| 5,096,867 | 3/1992 | Canich | 502/103 |
| 5,132,380 | 7/1992 | Stevens et al. | 526/126 |
| 5,470,993 | 11/1995 | Devore et al. | 556/11 |
| 5,532,394 | 7/1996 | Rosen et al. | 556/11 |
| 5,539,068 | 7/1996 | Devore et al. | 526/126 |
| 5,621,126 | 4/1997 | Canich et al. | 556/9 |
| 5,621,127 | 4/1997 | Langhauser et al. | 556/11 |
| 5,631,391 | 5/1997 | Canich | 556/11 |
| 5,688,880 | 11/1997 | Spencer et al. | 526/127 |
| 5,723,398 | 3/1998 | Rosen et al. | 502/103 |

FOREIGN PATENT DOCUMENTS

| A 416815 | 7/1990 | European Pat. Off. |
| WO 93/19104 | 1/1993 | WIPO |
| WO 95/14024 | 5/1995 | WIPO |
| WO 97 15583 | 5/1997 | WIPO |

*Primary Examiner*—Porfirio Nazario-Gonzalez

[57] ABSTRACT

Group 4 metal constrained geometry complexes comprising a fused ring indenyl derivative ligand, catalytic derivatives thereof, processes for preparing the same and their use as components of olefin polymerization catalysts are disclosed.

8 Claims, No Drawings

FUSED RING SUBSTITUTED INDENYL METAL COMPLEXES AND POLYMERIZATION PROCESS

CROSS-REFERENCE STATEMENT

This application claims the benefit of U.S. Provisional application Ser. No. 60/034,817 filed Dec. 19, 1996.

FIELD OF THE INVENTION

This invention relates to a class of Group 4 metal complexes and to polymerization catalysts derived therefrom that are particularly suitable for use in a polymerization process for preparing homopolymers and copolymers of olefins or diolefins, including copolymers comprising two or more olefins or diolefins such as copolymers comprising a monovinyl aromatic monomer and ethylene or copolymers comprising ethylene, propylene and a conjugated diene.

BACKGROUND

Constrained geometry metal complexes and methods for their preparation are disclosed in U.S. application Ser. No. 545,403, filed Jul. 3, 1990 (EP-A-416,815). This publication also teaches the preparation of certain novel copolymers of ethylene and a hindered vinyl monomer, including monovinyl aromatic monomers, having a pseudo-random incorporation of the hindered vinyl monomer therein. Additional teachings of constrained geometry catalysts may be found in U.S. application Ser. No. 547,718, filed Jul. 3, 1990 (EP-A-468,651); U.S. application Ser. No. 702,475, filed May 20, 1991 (EP-A-514,828); U.S. application Ser. No. 876,268, filed May 1, 1992, (EP-A-520,732) and U.S. application Ser. No. 8,003, filed Jan. 21, 1993 (WO93/19104), as well as U.S. Pat. Nos. 5,055,438, 5,057,475, 5,096,867, 5,064,802, 5,132,380, 5,470,993, WO95-00526, and U.S. Provisional Application 60-005913. Variously substituted indenyl containing metal complexes have been taught in U.S. Ser. No. 592,756, filed Jan. 26, 1996, as well as WO95/14024. The teachings of all of the foregoing patents or the corresponding U.S. patent applications are hereby incorporated by reference.

SUMMARY OF THE INVENTION

According to the present invention there are provided metal complexes corresponding to the formula (I):

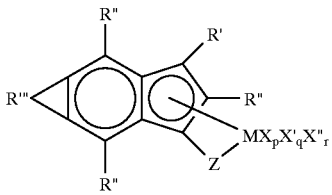

(I)

where M is titanium, zirconium or hafnium in the +2, +3 or +4 formal oxidation state;

R' and R" are independently each occurrence hydride, hydrocarbyl, silyl, germyl, halide, hydrocarbyloxy, hydrocarbylsiloxy, hydrocarbylsilylamino, di(hydrocarbyl)amino, hydrocarbyleneamino, di(hydrocarbyl)phosphino, hydrocarbylene-phosphino, hydrocarbylsulfido, halo-substituted hydrocarbyl, hydrocarbyloxy-substituted hydrocarbyl, silyl-substituted hydrocarbyl, hydrocarbylsiloxy-substituted hydrocarbyl, hydrocarbylsilylamino-substituted hydrocarbyl, di(hydrocarbyl)amino-substituted hydrocarbyl, hydrocarbyleneamino-substituted hydrocarbyl, di(hydrocarbyl)phosphino-substituted hydrocarbyl, hydrocarbylene-phosphino-substituted hydrocarbyl, or hydrocarbylsulfido-substituted hydrocarbyl, said R' or R" group having up to 40 nonhydrogen atoms, and optionally two or more of the foregoing groups may together form a divalent derivative;

R'" is a divalent hydrocarbylene- or substituted hydrocarbylene group forming a fused system with the remainder of the metal complex, said R'" containing from 1 to 30 nonhydrogen atoms;

Z is a divalent moiety, or a moiety comprising one a-bond and a neutral two electron pair able to form a coordinate-covalent bond to M, said Z comprising boron, or a member of Group 14 of the Periodic Table of the Elements, and also comprising nitrogen, phosphorus, sulfur or oxygen;

X is a monovalent anionic ligand group having up to 60 atoms exclusive of the class of ligands that are cyclic, delocalized, π-bound ligand groups;

X' independently each occurrence is a neutral ligating compound having up to 20 atoms;

X" is a divalent anionic ligand group having up to 60 atoms;

p is zero, 1, 2, or 3;

q is zero, 1 or 2, and r is zero or 1.

The above complexes may exist as isolated crystals optionally in pure form or as a mixture with other complexes, in the form of a solvated adduct, optionally in a solvent, especially an organic liquid, as well as in the form of a dimer or chelated derivative thereof, wherein the chelating agent is an organic material such as ethylenediaminetetraacetic acid (EDTA).

Also, according to the present invention, there is provided a catalyst for olefin polymerization comprising:

A. 1) a metal complex of formula (I), and
   2) an activating cocatalyst,
the molar ratio of 1) to 2) being from 1:10,000 to 100:1, or B. the reaction product formed by converting a metal complex of formula (I) to an active catalyst by use of an activating technique.

Further according to the present invention there is provided a process for the polymerization of olefins comprising contacting one or more $C_{2-20}$ α-olefins under polymerization conditions with a catalyst comprising:

A. 1) a metal complex of formula (I), and
   2) an activating cocatalyst,
the molar ratio of 1) to 2) being from 1:10,000 to 100:1, or B. the reaction product formed by converting a metal complex of formula (I) to an active catalyst by use of an activating technique.

Use of the present catalysts and processes results in the highly efficient production of high molecular weight olefin polymers over a wide range of polymerization conditions, and especially at elevated temperatures. They are especially useful for the formation of ethylene homopolymers, copolymers of ethylene and one or more α-olefins (i. e., olefins having greater than 3 carbon atoms), copolymers of ethylene, propylene and a diene (EPDM copolymers), copolymers of ethylene and styrene (ES polymers), copolymers of ethylene, styrene, and a diene (ESDM polymers), and copolymers of ethylene, propylene and styrene (EPS polymers). The use of the complexes, especially those wherein the metal is in the +2 formal oxidation state in continuous solution polymerizations surprisingly results in formation of polymers, especially EPDM terpolymers having extremely high molecular weights.

The catalysts of this invention may also be supported on a support material and used in olefin polymerization processes in a slurry or in the gas phase. The catalyst may be prepolymerized with one or more olefin monomers in situ in a polymerization reactor or in a separate process with intermediate recovery of the prepolymerized catalyst prior to the primary polymerization process.

The neutral diene complexes are prepared by contacting the corresponding complex in the +4 or +3 oxidation state with a neutral diene in the presence of a reducing agent, preferably a group 1 or 2 metal alkyl derivative having from 1 to 6 carbons in each alkyl group in an inert diluent. It has been found that the use of from 1.0 to 2.0 equivalents of the diene in the foregoing reaction gives improved yields and purity of the desired diene complex compared to the use of larger quantities of the diene. In addition, heating the reaction mixture prior to addition of the conjugated diene reactant, preferably to a temperature from 50 to 95° C., gives a further improvement in yield and purity.

DETAILED DESCRIPTION

All reference to the Periodic Table of the Elements herein shall refer to the Periodic Table of the Elements, published and copyrighted by CRC Press, Inc., 1995. Also, any reference to a Group or Groups shall be to the Group or Groups as reflected in this Periodic Table of the Elements using the IUPAC system for numbering groups.

Olefins as used herein are $C_{2-100,000}$ aliphatic or aromatic compounds containing vinylic unsaturation, as well as cyclic compounds such as cyclobutene, cyclopentene, and norbornene, including norbornene substituted in the 5 and 6 position with $C_{1-20}$ hydrocarbyl groups. Also included are mixtures of such olefins as well as mixtures of such olefins with $C_{4-40}$ diolefin compounds. Examples of the latter compounds include ethylidenenorbornene, 1,4-hexadiene, and norbornadiene. Long chain vinyl terminated monomers may be formed during the polymerization process, for example by the phenomenon of β-hydride elimination of a proton from a growing polymer chain. This process results in incorporation of extremely long chains into the resulting polymer, i. e. long chain branching. The catalysts and processes herein are especially suited for use in preparation of ethylene/propylene, ethylene/1-butene, ethylene/1-hexene, ethylene/styrene, and ethylene/1-octene copolymers as well as terpolymers of ethylene, propylene and a non-conjugated diene, referred to as EPDM polymers, terpolymers of ethylene, propylene and styrene, referred to as EPS polymers, or terpolymers of ethylene, styrene and a non-conjugated diene, referred to as ESDM polymers,.

Monovinyl aromatic monomers for use herein include $C_{8-20}$ aryl substituted ethylene compounds having the formula:

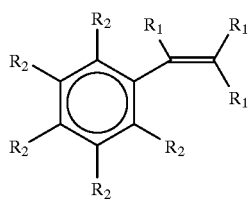

wherein:

$R_1$ independently each occurrence is hydrogen or $C_{1-4}$ alkyl, and $R_2$ independently each occurrence is $R_1$ or halo.

In the metal complexes, preferred X' groups are carbon monoxide; phosphines, especially trimethylphosphine, triethylphosphine, triphenylphosphine and bis(1,2-dimethylphosphino)ethane; $P(OR)_3$, wherein R is $C_{1-20}$ hydrocarbyl; ethers, especially tetrahydrofuran; amines, especially pyridine, bipyridine, tetramethylethylenediamine (TMEDA), and triethylamine; olefins; and neutral conjugated dienes having from 4 to 40 carbon atoms. Complexes including such neutral diene X' groups are those wherein the metal is in the +2 formal oxidation state.

Preferred R''' groups are those corresponding to the formula:

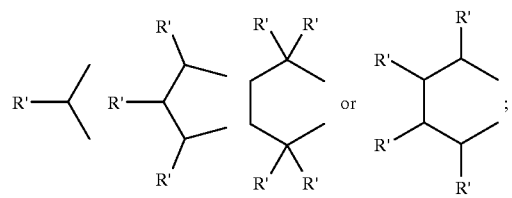

wherein R' is as previously defined, most preferably hydrogen or methyl.

Further in reference to the metal complexes, X preferably is selected from the group consisting of halo, hydrocarbyl, silyl, and N,N-dialkylamino substituted hydrocarbyl. The number of X groups depends on the oxidation state of M, whether Z is divalent or not and whether any neutral diene groups or divalent X'' groups are present. The skilled artisan will appreciate that the quantity of the various substituents and the identity of Z are chosen to provide charge balance, thereby resulting in a neutral metal complex. For example, when Z is divalent, and r is zero, p is two less than the formal oxidation state of M. When Z contains one neutral two electron coordinate-covalent bonding site, and M is in a formal oxidation state of +3, p may equal zero and r equal 1, or p may equal 2 and r equal zero. In a final example, if M is in a formal oxidation state of +2, Z may be a divalent ligand group, p and r may both equal zero and one neutral ligand group may be present.

Preferred coordination complexes used according to the present invention are complexes corresponding to the formula:

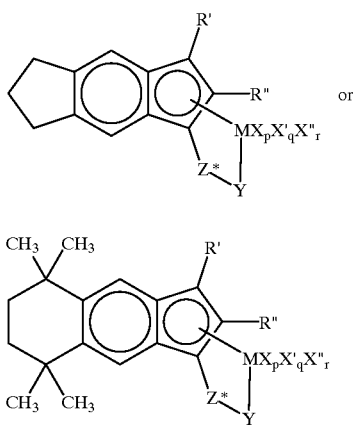

(II)

(III)

wherein:
R' is hydrocarbyl, di(hydrocarbylamino), or a hydrocarbyleneamino group, said R' having up to 20 carbon atoms, R" is $C_{1-20}$ hydrocarbyl or hydrogen;

M is titanium;

Y is —O—, —S—, —NR*—, —PR*—; —NR$_2$*, or —PR$_2$*;

Z* is SiR*$_2$, CR*$_2$, SiR*$_2$SiR*$_2$, CR*$_2$CR*$_2$, CR*=CR*, CR*$_2$SiR*$_2$, or GeR*$_2$;

R* each occurrence is independently hydrogen, or a member selected from hydrocarbyl, hydrocarbyloxy, silyl, halogenated alkyl, halogenated aryl, and combinations thereof, said R* having up to 20 non-hydrogen atoms, and optionally, two R* groups from Z (when R* is not hydrogen), or an R* group from Z and an R* group from Y form a ring system;

X, X' and X" are as previously defined;

p is 0, 1 or 2;

q is zero or 1; and r is zero or 1;

with the proviso that:
when p is 2, q and r are zero, M is in the +4 formal oxidation state (or M is in the +3 formal oxidation state if Y is —NR*$_2$ or —PR*$_2$), and X is an anionic ligand selected from the group consisting of halide, hydrocarbyl, hydrocarbyloxy, di(hydrocarbyl)amido, di(hydrocarbyl)phosphido, hydrocarbylsulfido, and silyl groups, as well as halo-, di(hydrocarbyl)amino-, hydrocarbyloxy-, and di(hydrocarbyl)phosphino-substituted derivatives thereof, said X group having up to 30 nonhydrogen atoms, when r is 1, p and q are zero, M is in the +4 formal oxidation state, and X" is a dianionic ligand selected from the group consisting of hydrocarbadiyl, oxyhydrocarbyl, and hydrocarbylenedioxy groups, said X group having up to 30 nonhydrogen atoms, when p is 1, q and r are zero, M is in the +3 formal oxidation state, and X is a stabilizing anionic ligand group selected from the group consisting of allyl, 2-(N,N-dimethylamino)phenyl, 2-(N,N-dimethylaminomethyl)phenyl, and 2-(N,N-dimethylamino)benzyl, and when p and r are zero, q is 1, M is in the +2 formal oxidation state, and X' is a neutral, conjugated or nonconjugated diene, optionally substituted with one or more hydrocarbyl groups, said X' having up to 40 carbon atoms and forming a 7π-complex with M.

Most preferred metal complexes are those according to the previous formula (II) or (III), wherein M, X, X', X", R' R", Z*, Y, p, q and r are as previously defined, with the proviso that:

when p is 2, q and r are zero, M is in the +4 formal oxidation state, and X is independently each occurrence methyl, benzyl, or halide;

when p and q are zero, r is one, and M is in the +4 formal oxidation state, X" is a 1,4-butadienyl group that forms a metallocyclopentene ring with M, when p is 1, q and r are zero, M is in the +3 formal oxidation state, and X is 2-(N,N-dimethylamino) benzyl; and when p and r are 0, q is 1, M is in the +2 formal oxidation state, and X' is 1,4-diphenyl-1,3-butadiene or 1,3-pentadiene.

Especially preferred coordination complexes corresponding to the previous formulas (II) and (III) are uniquely substituted depending on the particular end use thereof. In particular, highly useful metal complexes for use in catalyst compositions for the copolymerization of ethylene, one or more monovinyl aromatic monomers, and optionally an α-olefin or diolefin comprise the foregoing complexes (II) or (III) wherein R' is $C_{6-20}$ aryl, especially phenyl, biphenyl or naphthyl, and R" is hydrogen or methyl, especially hydrogen. More preferably such complexes are 3-phenyl-substituted s-indecenyl complexes corresponding to the formula:

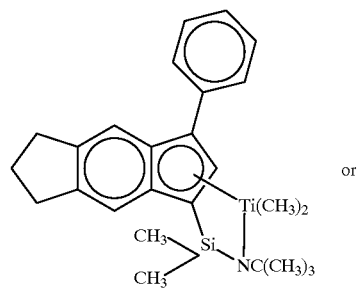

(IV)

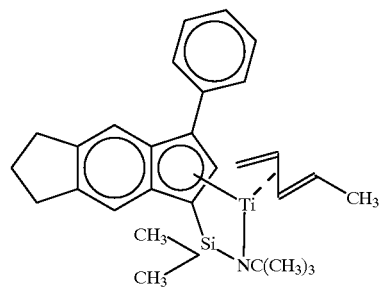

(V)

Highly useful metal complexes for use in catalyst compositions for the homopolymerization of ethylene or the copolymerization of ethylene and one or more α-olefins, especially 1-butene, 1-hexene or 1-octene, comprise the foregoing complexes (II) or (III) wherein R' is $C_{1-4}$ alkyl, N,N-dimethylamino or 1-pyrrolidinyl, and R" is hydrogen or $C_{1-4}$ alkyl. Moreover, in such complexes, Y is preferably a cyclohexylamido group, X is methyl, p is two, and both q and r are zero. Most preferably such complexes are 2,3- dimethyl-substituted s-indecenyl complexes corresponding to the formulas:

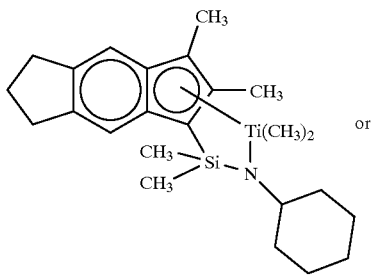

(VI)

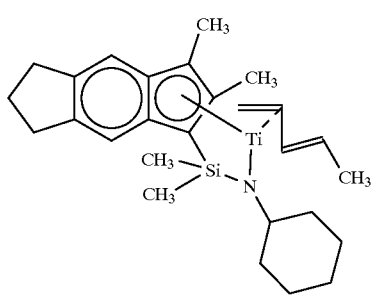

(VII)

Finally, highly useful metal complexes for use in catalyst compositions for the copolymerization of ethylene, an (α-olefin and a diene, especially ethylene, propylene and a nonconjugated diene, such as ethylidenenorbornene or 1,4-hexadiene, comprise the foregoing complexes (II) or (III) wherein R' is hydrogen, and R" is $C_{1-4}$ alkyl, especially methyl. Most preferred are 2-methyl-substituted s-indecenyl complexes corresponding to the formula:

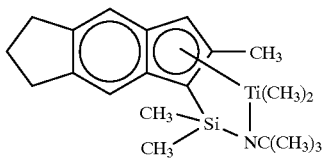

(VIII)

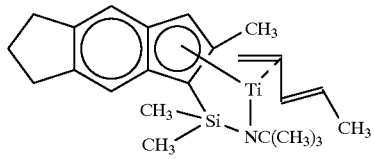

(IX)

Illustrative metal complexes that may be employed in the practice of the present invention include:

3-phenyl-s-indacen-1-yl complexes (alternatively referred to as [1,2,3,4,5-η)-1,5,6,7-tetrahydro-3-phenyl-s-indacen-1yl]complexes)

(t-butylamido)dimethyl($\eta^5$-3-phenyl-s-indacenyl) silanetitanium (II) 1,4-diphenyl-1,3-butadiene, (t-butylamido)dimethyl($\eta^5$-3-phenyl-s-indacenyl) silanetitanium(II) 1,3-pentadiene, (t-butylamido)dimethyl ($\eta^5$-3-phenyl-s-indacenyl)silanetitanium(III) 2-(N,N-dimethylamino)benzyl, (t-butylamido)dimethyl($\eta^5$-3-phenyl-s-indacenyl)silanetitanium(IV) dimethyl, (t-butylamido)dimethyl($\eta^5$-3-phenyl-s-indacenyl) silanetitanium(IV) dibenzyl, (i-propylamido)dimethyl($\eta^5$-3-phenyl-s-indacenyl)silanetitanium(IV) dimethyl, (benzylamido)dimethyl($\eta$5-3-phenyl-s-indacenyl) silanetitanium(IV) dimethyl, (cyclohexylamido)dimethyl ($\eta^5$-3-phenyl-s-indacenyl)silanetitanium(IV) dimethyl, (n-butylamido)dimethyl($\eta^5$-3-phenyl-s-indacenyl) silanetitanium(II) 1,4-diphenyl-1,3-butadiene, (n-butylamido)dimethyl($\eta^5$-3-phenyl-s-indacenyl) silanetitanium(II) 1,3-pentadiene, (n-butylamido)dimethyl ($\eta^5$-3-phenyl-s-indacenyl)silanetitanium(III) 2-(N,N-dimethylamino)benzyl, (n-butylamido)dimethyl($\eta^5$-3-phenyl-s-indacenyl)silanetitanium(IV) dimethyl, (n-butylamido)dimethyl($\eta$5-3-phenyl-s-indacenyl) silanetitanium(IV) dibenzyl, (cyclododecylamido)dimethyl($\eta^5$-3-phenyl-s-indacenyl) silanetitanium(II) 1,4-diphenyl-1,3-butadiene, (cyclododecylamido)dimethyl($\eta^5$-3-phenyl-s-indacenyl) silanetitanium(II) 1,3-pentadiene, (cyclododecylamido) dimethyl($\eta^5$-3-phenyl-s-indacenyl)silanetitanium(III) 2-(N, N-dimethylamino)benzyl, (cyclododecylamido)dimethyl ($\eta^5$-3-phenyl-s-indacenyl)silanetitanium(IV) dimethyl, (cyclododecylamido)dimethyl($\eta^5$-3-phenyl-s-indacenyl) silanetitanium(IV) dibenzyl, (2,4,6-trimethylanilido)dimethyl($\eta^5$-3-phenyl-s-indacenyl)silanetitanium(II) 1,4-diphenyl-1,3-butadiene, (2,4,6-trimethylanilido)dimethyl-($\eta^5$-3-phenyl-s-indacenyl) silanetitanium(II) 1,3-pentadiene, (2,4,6-trimethylanilido) dimethyl($\eta^5$-3-phenyl-s-indacenyl)silanetitanium (III) 2-(N, N-dimethylamino)benzyl, (2,4,6-trimethylanilido)dimethyl ($\eta^5$-3-phenyl-s-indacenyl)silanetitanium(IV) dimethyl, (2,4, 6-trimethylanilido)dimethyl($\eta^5$-3-phenyl-s-indacenyl) silanetitanium(IV) dibenzyl, (t-butylamido)dimethoxy($\eta^5$-3-phenyl-s-indacenyl) silanetitanium (II) 1,4-diphenyl-1,3-butadiene, (t-butylamido)dimethoxy($\eta^5$-3-phenyl-s-indacenyl) silanetitanium(II) 1,3-pentadiene, (t-butylamido)dimethoxy ($\eta^5$-3-phenyl-s-indacenyl)silanetitanium(III) 2-(N,N-dimethylamino)benzyl, (t-butylamido)dimethoxy($\eta^5$-3-phenyl-s-indacenyl)silanetitanium(IV) dimethyl, and (t-butylamido)dimethoxy($\eta^5$-3-phenyl-s-indacenyl) silanetitanium(IV) dibenzyl.

3-naphthyl-s-indacenyl complexes (t-butylamido)dimethyl($\eta^5$-3-naphthyl-s-indacenyl) silanetitanium (II) 1,4-diphenyl-1,3-butadiene, (t-butylamido)dimethyl($\eta^5$-3-naphthyl-s-indacenyl) silanetitanium (II) 1,3-pentadiene, (t-butylamido)dimethyl ($\eta^5$-3-naphthyl-s-indacenyl)silanetitanium (III) 2-(N,N-dimethylamino)benzyl, (t-butylamido)dimethyl($\eta^5$-3-naphthyl-s-indacenyl)silanetitanium (IV) dimethyl, (t-butylamido)dimethyl($\eta^5$-3-naphthyl-s-indacenyl) silanetitanium (IV) dibenzyl (i-propylamido)dimethyl($\eta^5$-3-naphthyl-s-indacenyl)silanetitanium (IV) dimethyl (benzylamido)dimethyl($\eta^5$-3-naphthyl-s-indacenyl) silanetitanium (IV) dimethyl, and (cyclohexylamido) dimethyl($\eta^5$-3-naphthyl-s-indacenyl)silanetitanium (IV) dimethyl 3-biphenyl-s-indacenyl complexes (t-butylamido)dimethyl($\eta^5$-3-biphenyl-s-indacenyl) silanetitanium (II) 1,4-diphenyl-1,3-butadiene, (t-butylamido)dimethyl($\eta^5$-3-biphenyl-s-indacenyl) silanetitanium (II) 1,3-pentadiene, (t-butylamido)dimethyl ($\eta^5$-3-biphenyl-s-indacenyl)silanetitanium (III) 2-(N,N-dimethylamino)benzyl, (t-butylamido)dimethyl($\eta^5$-3- biphenyl-s-indacenyl)silanetitanium (IV) dimethyl, (t-butylamido)dimethyl($\eta^5$-3-biphenyl-s-indacenyl)silanetitanium (IV) dibenzyl (i-propylamido)dimethyl($\eta^5$-3-biphenyl-s-indacenyl)silanetitanium (IV) dimethyl (benzylamido)dimethyl($\eta^5$-3-biphenyl-s-indacenyl) silanetitanium (IV) dimethyl, and (cyclohexylamido)dimethyl($\eta^5$-3-biphenyl-s-indacenyl)silanetitanium (IV) dimethyl 2-methyl-3-phenyl-s-indacenyl complexes (t-butylamido)dimethyl($\eta$5-2-methyl-3-phenyl-s-indacenyl)silanetitanium (II) 1,4-diphenyl-1,3-butadiene, (t-butylamido)dimethyl($\eta$5-2-methyl-3-phenyl-s-indacenyl)silanetitanium (II) 1,3-pentadiene, (t-butylamido)dimethyl ($\eta^5$-2-methyl-3-phenyl-s-indacenyl)silanetitanium (III) 2-(N,N-dimethylamino)benzyl, (t-butylamido)dimethyl($\eta^5$-2-methyl-3-phenyl-s-indacenyl)silanetitanium (IV) dimethyl, and (t-butylamido)dimethyl($\eta^5$-2-methyl-3-phenyl-s-indacenyl)silanetitanium (IV) dibenzyl.

2-methyl-3-biphenyl-s-indacenyl complexes (t-butylamido)dimethyl($\eta^5$-2-methyl-3-biphenyl-s-indacenyl)silane-titanium (II) 1,4-diphenyl-1,3-butadiene, (t-butylamido)dimethyl($\eta^5$-2-methyl-3-biphenyl-s-indacenyl)silane-titanium (II) 1,3-pentadiene, (t-butylamido)dimethyl($\eta^5$-2-methyl-3-biphenyl-s-indacenyl)silane-titanium (III) 2-(N,N-dimethylamino)benzyl, (t-butylamido)dimethyl($\eta^5$-2-methyl-3-biphenyl-s-indacenyl)silane-titanium (IV) dimethyl, (t-butylamido)dimethyl($\eta^5$-2-methyl-3-biphenyl-s-indacenyl)silane-titanium (IV) dibenzyl (i-propylamido)dimethyl($\eta^5$-2-methyl-3-biphenyl-s-indacenyl)silane-titanium (IV) dimethyl (benzylamido)dimethyl($\eta^5$-2-methyl-3-biphenyl-s-indacenyl)silane-titanium (IV) dimethyl, and (cyclohexylamido)dimethyl($\eta^5$-2-methyl-3-biphenyl-s-indacenyl)silane-titanium (IV) dimethyl 2-methyl-3-naphthyl-s-indacenyl complexes (t-butylamido)dimethyl($\eta^5$-2-methyl-3-naphthyl-s-indacenyl)silanetitanium (II) 1,4-diphenyl-1,3-butadiene, (t-butylamido)dimethyl($\eta^5$-2-methyl-3-naphthyl-s-indacenyl)silanetitanium(II) 1,3-pentadiene, (t-butylamido)dimethyl($\eta^5$-2-methyl-3-naphthyl-s-indacenyl)silanetitanium(III) 2-(N,N-dimethylamino)benzyl, (t-butylamido)dimethyl($\eta^5$-2-methyl-3-naphthyl-s-indacenyl)silanetitanium(IV) dimethyl, (t-butylamido)dimethyl($\eta^5$-2-methyl-3-naphthyl-s-indacenyl)silanetitanium(IV) dibenzyl, (cyclohexylamido)dimethyl($\eta^5$-2-methyl-3-naphthyl-s-indacenyl)silanetitanium (II) 1,4-diphenyl-1,3-butadiene, (cyclohexylamido)dimethyl($\eta^5$-2-methyl-3-naphthyl-s-indacenyl)silanetitanium (II) 1,3-pentadiene, (cyclohexylamido)dimethyl($\eta^5$-2-methyl-3-naphthyl-s-indacenyl)silanetitanium (III) 2-(N,N-dimethylamino)benzyl, (cyclohexylamido)dimethyl($\eta^5$-2-methyl-3-naphthyl-s-indacenyl)silanetitanium (IV) dimethyl, and (cyclohexylamido)dimethyl($\eta^5$-2-methyl-3-naphthyl-s-indacenyl)silanetitanium (IV) dibenzyl.

2-methyl-s-indacenyl complexes (t-butylamido)dimethyl($\eta^5$-2-methyl-s-indacenyl)silanetitanium (II) 1,4-diphenyl-1,3-butadiene, (t-butylamido)dimethyl($\eta^5$-2-methyl-s-indacenyl)silanetitanium(II) 1,3-pentadiene, (t-butylamido)dimethyl ($\eta^5$-2-methyl-s-indacenyl)silanetitanium(III) 2-(N,N-dimethylamino)benzyl, (t-butylamido)dimethyl($\eta^5$-2-methyl-s-indacenyl)silanetitanium(IV) dimethyl, (t-butylamido)dimethyl($\eta$5-2-methyl-s-indacenyl)silanetitanium(IV) dibenzyl, (cyclohexylamido)dimethyl ($\eta^5$-2-methyl-s-indacenyl)silanetitanium (II) 1,4-diphenyl-1,3-butadiene, (cyclohexylamido)dimethyl($\eta^5$-2-methyl-s-indacenyl)silanetitanium (II) 1,3-pentadiene, (cyclohexylamido)dimethyl($\eta^5$-2-methyl-s-indacenyl)silanetitanium (III) 2-(N,N-dimethylamino)benzyl, (cyclohexylamido)dimethyl($\eta^5$-2-methyl-s-indacenyl)silanetitanium (IV) dimethyl, and (cyclohexylamido)dimethyl($\eta^5$-2-methyl-s-indacenyl)silanetitanium (IV) dibenzyl.

2,3-dimethyl-s-indacenyl complexes (t-butylamido)dimethyl($\eta^5$-2,3-dimethyl-s-indacenyl)silanetitanium (II) 1,4-diphenyl-1,3-butadiene, (t-butylamido)dimethyl($\eta^5$-2,3-dimethyl-s-indacenyl)silanetitanium(II) 1,3-pentadiene, (t-butylamido)dimethyl ($\eta^5$-2,3-dimethyl-s-indacenyl)silanetitanium(III) 2-(N,N-dimethylamino)benzyl, (t-butylamido)dimethyl($\eta^5$-2,3-dimethyl-s-indacenyl)silanetitanium(IV) dimethyl, (t-butylamido)dimethyl($\eta^5$-2,3-dimethyl-s-indacenyl)silanetitanium(IV) dibenzyl, (cyclohexylamido)dimethyl ($\eta^5$-2,3-dimethyl-s-indacenyl)silanetitanium (II) 1,4-diphenyl-1,3-butadiene, (cyclohexylamido)dimethyl($\eta^5$-2,3-dimethyl-s-indacenyl)silanetitanium (II) 1,3-pentadiene, (cyclohexylamido)dimethyl($\eta^5$-2,3-dimethyl-s-indacenyl)silanetitanium (III) 2-(N,N-dimethylamino)benzyl, (cyclohexylamido)dimethyl($\eta^5$-2,3-dimethyl-s-indacenyl)silanetitanium (IV) dimethyl, and (cyclohexylamido)dimethyl($\eta^5$-2,3-dimethyl-s-indacenyl)silanetitanium (IV) dibenzyl.

3-phenyl-gem-dimethylacenaphthalenyl complexes
(also referred to as (1,2,3,4,5-$\eta$)(5,6,7,8-tetrahydro-5,5,8,8-tetramethyl-1H-Benz(f)inde-1-complexes)

(t-butylamido)dimethyl($\eta^5$-3-phenyl-gem-dimethylacenaphth-alenyl)silanetitanium (II) 1,4-diphenyl-1,3-butadiene, (t-butylamido)dimethyl($\eta^5$-3-phenyl-gem-dimethylacenaphth-alenyl)silanetitanium(II) 1,3-pentadiene, (t-butylamido)dimethyl($\eta^5$-3-phenyl-gem-dimethylacenaphth-alenyl)silanetitanium(III) 2-(N,N-dimethylamino)benzyl, (t-butylamido)dimethyl($\eta^5$-3-phenyl-gem-dimethylacenaphth-alenyl)silanetitanium(IV) dimethyl, (t-butylamido)dimethyl($\eta^5$-3-phenyl-gem-dimethylacenaphth-alenyl)silanetitanium(IV) dibenzyl, (n-butylamido)dimethyl($\eta^5$-3-phenyl-gem-dimethylacenaphth-alenyl)silanetitanium(II) 1,4-diphenyl-1,3-butadiene, (n-butylamido)dimethyl($\eta^5$-3-phenyl-gem-dimethylacenaphth-alenyl)silanetitanium(II) 1,3-pentadiene, (n-butylamido)dimethyl($\eta^5$-3-phenyl-gem-dimethylacenaphth-alenyl)silanetitanium(III) 2-(N,N-dimethylamino)benzyl, (n-butylamido)dimethyl($\eta^5$-3-phenyl-gem-dimethylacenaphth-alenyl)silanetitanium(IV) dimethyl, (n-butylamido)dimethyl($\eta^5$-3-phenyl-gem-dimethylacenaphth-alenyl)silanetitanium(IV) dibenzyl, (cyclododecylamido)dimethyl($\eta^5$-3-phenyl-gem-dimethylacenaphth-alenyl)silanetitanium(II) 1,4-diphenyl-1,3-butadiene, (cyclododecylamido)dimethyl($\eta^5$-3-phenyl-gem-dimethylacenaphth-alenyl)silanetitanium(II) 1,3-pentadiene, (cyclododecylamido)dimethyl($\eta^5$-3-phenyl-gem-dimethylacenaphth-alenyl)silanetitanium(III) 2-(N,N-dimethylamino)benzyl, (cyclododecylamido)dimethyl($\eta^5$-3-phenyl-gem-dimethylacenaphth-alenyl)silanetitanium (IV) dimethyl, (cyclododecylamido)dimethyl($\eta^5$-3-phenyl-gem-dimethylacenaphth-alenyl)silanetitanium(IV) dibenzyl, (2,4,6-trimethylanilido)dimethyl($\eta^5$-3-phenyl-gem-dimethylacenaphth-alenyl)silanetitanium(II) 1,4-diphenyl-1,3-butadiene, (2,4,6-trimethylanilido)dimethyl($\eta^5$-3-phenyl-gem-dimethylacenaphth-alenyl)silanetitanium(II) 1,3-pentadiene, (2,4,6-trimethylanilido)dimethyl($\eta^5$-3-phenyl-gem-dimethylacenaphth-alenyl)silanetitanium (III) 2-(N,N-dimethylamino)benzyl, (2,4,6-trimethylanilido) dimethyl($\eta^5$-3-phenyl-gem-dimethylacenaphth-alenyl) silanetitanium(IV) dimethyl, (2,4,6-trimethylanilido) dimethyl($\eta^5$-3-phenyl-gem-dimethylacenaphth-alenyl) silanetitanium(IV) dibenzyl, (t-butylamido)dimethoxy($\eta^5$-3-phenyl-gem-dimethylacenaphth-alenyl)silanetitanium(II) 1,4-diphenyl-1,3-butadiene, (t-butylamido)dimethoxy($\eta^5$-3-phenyl-gem-dimethylacenaphth-alenyl)silanetitanium(II) 1,3-pentadiene, (t-butylamido)dimethoxy($\eta^5$-3-phenyl-gem-dimethylacenaphth-alenyl)silanetitanium(III) 2-(N,N-dimethylamino)benzyl, (t-butylamido)dimethoxy($\eta^5$-3-phenyl-gem-dimethylacenaphth-alenyl)silanetitanium(IV) dimethyl, and (t-butylamido)dimethoxy($\eta^5$-3-phenyl-gem-dimethylacenaphth-alenyl)silanetitanium(IV) dibenzyl.

3-naphthyl-gem-dimethylacenaphthalenyl complexes (t-butylamido)dimethyl($\eta^5$-3-naphthyl-gem-dimethylacenaphth-alenyl)silanetitanium (II) 1,4-diphenyl-1,3-butadiene, (t-butylamido)dimethyl($\eta^5$-3-naphthyl-gem-dimethylacenaphth-alenyl)silanetitanium (II) 1,3-pentadiene, (t-butylamido)dimethyl($\eta^5$-3-naphthyl-gem-dimethylacenaphth-alenyl)silanetitanium (III) 2-(N,N-dimethylamino)benzyl, (t-butylamido)dimethyl($\eta^5$-3-naphthyl-gem-dimethylacenaphth-alenyl)silanetitanium (IV) dimethyl, and (t-butylamido)dimethyl($\eta^5$-3-naphthyl-gem-dimethylacenaphth-alenyl)silanetitanium (IV) dibenzyl

3-biphenyl-gem-dimethylacenaphthalenyl complexes (t-butylamido)dimethyl($\eta^5$-3-biphenyl-gem-dimethylacenaphth-alenyl)silanetitanium (II) 1,4-diphenyl, 1,3-butadiene, (t-butylamido)dimethyl($\eta^5$-3-biphenyl-gem-dimethylacenaphth-alenyl)silanetitanium (II) 1,3-pentadiene, (t-butylamido)dimethyl($\eta^5$-3-biphenyl-gem-dimethylacenaphth-alenyl)silanetitanium (III) 2-(N,N-dimethylamino)benzyl, (t-butylamido)dimethyl($\eta^5$-3-biphenyl-gem-dimethylacenaphth-alenyl)silanetitanium (IV) dimethyl, and (t-butylamido)dimethyl($\eta^5$-3-biphenyl-gem-dimethylacenaphth-alenyl)silanetitanium (IV) dibenzyl

2-methyl-3-phenyl-gem-dimethylacenaphthalenyl complexes (t-butylamido)dimethyl($\eta^5$-2-methyl-3-phenyl-gem-dimethylacenaphth-alenyl)silanetitanium (II) 1,4-diphenyl-1,3-butadiene, (t-butylamido)dimethyl($\eta^5$-2-methyl-3-phenyl-gem-dimethylacenaphth-alenyl)silanetitanium (II) 1,3-pentadiene, (t-butylamido)dimethyl($\eta^5$-2-methyl-3-phenyl-gem-dimethylacenaphth-alenyl)silanetitanium (III) 2-(N,N-dimethylamino)benzyl, (t-butylamido)dimethyl($\eta^5$-2-methyl-3-phenyl-gem-dimethylacenaphth-alenyl) silanetitanium (IV) dimethyl, and (t-butylamido)dimethyl ($\eta^5$-2-methyl-3-phenyl-gem-dimethylacenaphth-alenyl) silanetitanium (IV) dibenzyl.

The complexes can be prepared by use of well known synthetic techniques. Optionally a reducing agent can be employed to produce the lower oxidation state complexes. Such a process is disclosed in U.S. Ser. No. 8/241,523, filed May 13, 1994, published as WO 95-00526, the teachings of which are hereby incorporated by reference. The syntheses are conducted in a suitable noninterfering solvent at a temperature from −100 to 300° C., preferably from −78 to 100° C., most preferably from 0 to 50° C. By the term "reducing agent" herein is meant a metal or compound which, under reducing conditions causes the metal M, to be reduced from a higher to a lower oxidation state. Examples of suitable metal reducing agents are alkali metals, alkaline earth metals, aluminum and zinc, alloys of alkali metals or alkaline earth metals such as sodium/mercury amalgam and sodium/potassium alloy. Examples of suitable reducing agent compounds are group 1 or 2 metal hydrocarbyl compounds having from 1 to 20 carbons in each hydrocarbyl group, such as, sodium naphthalenide, potassium graphite, lithium alkyls, lithium or potassium alkadienyls; and Grignard reagents. Most preferred reducing agents are the alkali metals or alkaline earth metals, especially lithium and magnesium metal.

Suitable reaction media for the formation of the complexes include aliphatic and aromatic hydrocarbons, ethers, and cyclic ethers, particularly branched-chain hydrocarbons such as isobutane, butane, pentane, hexane, heptane, octane, and mixtures thereof; cyclic and alicyclic hydrocarbons such as cyclohexane, cycloheptane, methylcyclohexane, methylcycloheptane, and mixtures thereof; aromatic and hydrocarbyl-substituted aromatic compounds such as benzene, toluene, and xylene, $C_{1-4}$ dialkyl ethers, $C_{1-4}$ dialkyl ether derivatives of (poly)alkylene glycols, and tetrahydrofuran. Mixtures of the foregoing are also suitable.

As previously mentioned, the diene complexes wherein the metal is in the +2 formal oxidation state can be conveniently prepared by reaction of the corresponding metal complex wherein the metal is in the +3 or +4 formal oxidation state, especially the dihalide complex, with the neutral diene in the presence of a reducing agent. In a preferred embodiment, it has been discovered that a large excess of diene reactant is detrimental to this reaction. Accordingly, in a preferred embodiment there is provided a process for preparing a neutral diene complex corresponding to the formula:

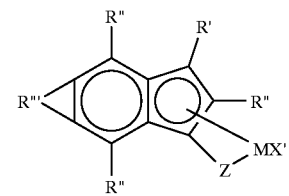

where M is titanium in the +2 formal oxidation state;
R' and R" are independently each occurrence hydride, hydrocarbyl, silyl, germyl, halide, hydrocarbyloxy, hydrocarbylsiloxy, hydrocarbylsilylamino, di(hydrocarbyl)amino, hydrocarbyleneamino, di(hydrocarbyl)phosphino, hydrocarbylene-phosphino, hydrocarbylsulfido, halo-substituted hydrocarbyl, hydrocarbyloxy-substituted hydrocarbyl, silyl-substituted hydrocarbyl, hydrocarbylsiloxy-substituted hydrocarbyl, hydrocarbylsilylamino-substituted hydrocarbyl, di(hydrocarbyl)amino-substituted hydrocarbyl, hydrocarbyleneamino-substituted hydrocarbyl, di(hydrocarbyl)phosphino-substituted hydrocarbyl, hydrocarbylene-phosphino-substituted hydrocarbyl, or hydrocarbylsulfido-substituted hydrocarbyl, said R' or R" group having up to 40 nonhydrogen atoms, and optionally two or more of the foregoing groups may together form a divalent derivative;

R''' is a divalent hydrocarbylene- or substituted hydrocarbylene group forming a fused system with the remainder of the metal complex, said R''' containing from 1 to 30 nonhydrogen atoms;

Z is a divalent moiety, or a moiety comprising one a-bond and a neutral two electron pair able to form a coordinate-covalent bond to M, said Z comprising boron, or a member of Group 14 of the Periodic Table of the Elements, and also comprising nitrogen, phosphorus, sulfur or oxygen; and X' independently is a neutral conjugated diene compound having up to 20 carbon atoms;

comprising contacting a metal complex corresponding to the formula:

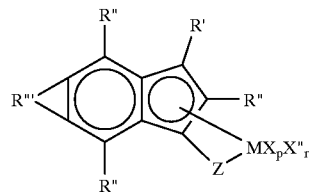

where M is titanium in the +3 or +4 formal oxidation state;

R', R'', R''', and Z are as previously defined;

X is a monovalent anionic ligand group having up to 60 atoms exclusive of the class of ligands that are cyclic, delocalized, π-bound ligand groups;

X'' is a divalent anionic ligand group having up to 60 atoms;

p is 1, or 2; and r is zero or 1 with from 1 to 2 equivalents of a neutral conjugated diene of the formula X' in an inert diluent in the presence of a reducing agent and recovering the resulting product.

In another preferred embodiment of the process, the reagents are contacted at an elevated temperature from 50 to 95° C. rather than first contacting the reagent sat a lower temperature and then raising the reaction temperature. More particularly, it is desirable to conduct the process under conditions wherein a reaction mixture comprising the metal complex and reducing agent is heated to a temperature from 50 to 95° C. prior to adding the conjugated diene.

The complexes are rendered catalytically active by combination with an activating cocatalyst or by use of an activating technique. Suitable activating cocatalysts for use herein include polymeric or oligomeric alumoxanes, especially methylalumoxane, triisobutyl aluminum modified methylalumoxane, or isobutylalumoxane; neutral Lewis acids, such as $C_{1-30}$ hydrocarbyl substituted Group 13 compounds, especially tri(hydrocarbyl)aluminum- or tri(hydrocarbyl)boron compounds and halogenated (including perhalogenated) derivatives thereof, having from 1 to 10 carbons in each hydrocarbyl or halogenated hydrocarbyl group, more especially perfluorinated tri(aryl)boron compounds, and most especially tris(pentafluorophenyl) borane; nonpolymeric, compatible, noncoordinating, ion forming compounds (including the use of such compounds under oxidizing conditions), especially the use of ammonium-, phosphonium-, oxonium-, carbonium-, silylium- or sulfonium- salts of compatible, noncoordinating anions, or ferrocenium salts of compatible, noncoordinating anions; bulk electrolysis (explained in more detail hereinafter); and combinations of the foregoing activating cocatalysts and techniques. The foregoing activating cocatalysts and activating techniques have been previously taught with respect to different metal complexes in the following references: EP-A-277,003, U.S. Pat. Nos. 5,153,157, 5,064, 802, EP-A-468,651 (equivalent to U.S. Ser. No. 07/547, 718), EP-A-520,732 (equivalent to U.S. Ser. No. 07/876, 268), and EP-A-520,732 (equivalent to U.S. Ser. No. 07/884,966 filed May 1, 1992), the teachings of which are hereby incorporated by reference.

Combinations of neutral Lewis acids, especially the combination of a trialkylaluminum compound having from 1 to 4 carbons in each alkyl group and a halogenated tri(hydrocarbyl)boron compound having from 1 to 20 carbons in each hydrocarbyl group, especially tris (pentafluorophenyl)borane, further combinations of such neutral Lewis acid mixtures with a polymeric or oligomeric alumoxane, and combinations of a single neutral Lewis acid, especially tris(pentafluorophenyl)borane with a polymeric or oligomeric alumoxane are especially desirable activating cocatalysts. Preferred molar ratios of Group 4 metal complex:tris(pentafluoro-phenylborane:alumoxane are from 1:1:1 to 1:10:30, more preferably from 1:1:1.5 to 1:5:10.

Suitable ion forming compounds useful as cocatalysts in one embodiment of the present invention comprise a cation which is a Bronsted acid capable of donating a proton, and a compatible, noncoordinating anion, AK. As used herein, the term "noncoordinating" means an anion or substance which either does not coordinate to the Group 4 metal containing precursor complex and the catalytic derivative derived therefrom, or which is only weakly coordinated to such complexes thereby remaining sufficiently labile to be displaced by a neutral Lewis base. A noncoordinating anion specifically refers to an anion which when functioning as a charge balancing anion in a cationic metal complex does not transfer an anionic substituent or fragment thereof to said cation thereby forming neutral complexes. "Compatible anions" are anions which are not degraded to neutrality when the initially formed complex decomposes and are noninterfering with desired subsequent polymerization or other uses of the complex.

Preferred anions are those containing a single coordination complex comprising a charge-bearing metal or metalloid core which anion is capable of balancing the charge of the active catalyst species (the metal cation) which may be formed when the two components are combined. Also, said anion should be sufficiently labile to be displaced by olefinic, diolefinic and acetylenically unsaturated compounds or other neutral Lewis bases such as ethers or nitriles. Suitable metals include, but are not limited to, aluminum, gold and platinum. Suitable metalloids include, but are not limited to, boron, phosphorus, and silicon. Compounds containing anions which comprise coordination complexes containing a single metal or metalloid atom are, of course, well known and many, particularly such compounds containing a single boron atom in the anion portion, are available commercially.

Preferably such cocatalysts may be represented by the following general formula:

$$(L^*-H)_d^+(A)^{d-}$$

wherein:

L* is a neutral Lewis base;

$(L^*-H)^+$ is a conjugate Bronsted acid of L*;

$A^{d-}$ is a noncoordinating, compatible anion having a charge of d−, and d is an integer from 1 to 3.

More preferably $A^{d-}$ corresponds to the formula: $[M'Q_4]^-$; wherein:

M' is boron or aluminum in the +3 formal oxidation state; and

Q independently each occurrence is selected from hydride, dialkylamido, halide, hydrocarbyl, hydrocarbyloxide, halo-substituted hydrocarbyl, halo-substituted hydrocarbyloxy, and halo- substituted silyl-hydrocarbyl radicals (including perhalogenated hydrocarbyl-perhalogenated hydrocarbyloxy- and perhalogenated silylhydrocarbyl radicals), said Q having up to 20 carbons with the proviso that in not more than one occurrence is Q halide. Examples of suitable hydrocarbyloxide Q groups are disclosed in U.S. Pat. No. 5,296,433, the teachings of which are herein incorporated by reference.

In a more preferred embodiment, d is one, that is, the counter ion has a single negative charge and is $A^-$. Activating cocatalysts comprising boron which are particularly useful in the preparation of catalysts of this invention may be represented by the following general formula:

$$(L^*-H)^+(BQ_4)^-;$$

wherein:

L* is as previously defined;

B is boron in a formal oxidation state of 3; and

Q is a hydrocarbyl-, hydrocarbyloxy-, fluorinated hydrocarbyl-, fluorinated hydrocarbyloxy-, or fluorinated silylhydrocarbyl- group of up to 20 nonhydrogen atoms, with the proviso that in not more than one occasion is Q hydrocarbyl.

Preferred Lewis base salts are ammonium salts, more preferably trialkylammonium salts containing one or more $C_{12-40}$ alkyl groups. Most preferably, Q is each occurrence a fluorinated aryl group, especially, a pentafluorophenyl group.

Illustrative, but not limiting, examples of boron compounds which may be used as an activating cocatalyst in the preparation of the improved catalysts of this invention are tri-substituted ammonium salts such as:
trimethylammonium tetrakis(pentafluorophenyl) borate,
triethylammonium tetrakis(pentafluorophenyl) borate,
tripropylammonium tetrakis(pentafluorophenyl) borate,
tri (n-butyl)ammonium tetrakis(pentafl uorophenyl) borate,
tri(sec-butyl)ammonium tetrakis(pentafluorophenyl) borate,
N,N-dimethylanilinium tetrakis(pentafluorophenyl) borate,
N,N-dimethylanilinium n-butyltris(pentafluorophenyl) borate,
N,N-dimethylanilinium benzyltris(pentafluorophenyl) borate,
N,N-dimethylanilinium tetrakis(4-(t-butyldimethylsilyl)-2, 3, 5, 6-tetrafluorophenyl) borate,
N,N-dimethylanilinium tetrakis(4-(triisopropylsilyl)-2, 3, 5, 6-tetrafluorophenyl) borate,
N,N-dimethylanilinium pentafluorophenoxytris (pentafluorophenyl) borate,
N,N-diethylanilinium tetrakis(pentafluorophenyl) borate,
N,N-dimethyl-2,4,6-trimethylanilinium tetrakis (pentafluorophenyl) borate,
dimethyloctadecylammonium tetrakis (pentafluorophenyl) borate,
methyldioctadecylammonium tetrakis (pentafluorophenyl) borate, dialkyl ammonium salts such as:
di-(i-propyl)ammonium tetrakis(pentafluorophenyl) borate,
methyloctadecylammonium tetrakis (pentafluorophenyl) borate,
methyloctadodecylammonium tetrakis (pentafluorophenyl) borate, and
dioctadecylammonium tetrakis(pentafluorophenyl) borate;

tri-substituted phosphonium salts such as:
triphenylphosphonium tetrakis(pentafluorophenyl) borate,
methyldioctadecylphosphonium tetrakis (pentafluorophenyl) borate, and
tri(2,6-dimethylphenyl)phosphonium tetrakis (pentafluorophenyl) borate;

di-substituted oxonium salts such as:
diphenyloxonium tetrakis(pentafluorophenyl) borate,
di(o-tolyl)oxonium tetrakis(pentafluorophenyl) borate, and
di(octadecyl)oxonium tetrakis(pentafluorophenyl) borate;

di-substituted sulfonium salts such as:
di(o-tolyl)sulfonium tetrakis(pentafluorophenyl) borate, and
methylcotadecy lsulfonium tetrakis(pentafluorophenyl) borate.

Preferred $(L^*-H)^+$ cations are methyldioctadecylammonium and dimethyloctadecylammonium.

Another suitable ion forming, activating cocatalyst comprises a salt of a cationic oxidizing agent and a noncoordinating, compatible anion represented by the formula:

$$(Ox^{e+})_d(A^{d-})_e.$$

wherein:

$Ox^{e+}$ is a cationic oxidizing agent having a charge of e+;

e is an integer from 1 to 3; and $A^{d-}$ and d are as previously defined.

Examples of cationic oxidizing agents include: ferrocenium, hydrocarbyl-substituted ferrocenium, $Ag^+$, or $Pb^{+2}$. Preferred embodiments of $A^{d-}$ are those anions previously defined with respect to the Bronsted acid containing activating cocatalysts, especially tetrakis (pentafluorophenyl)borate.

Another suitable ion forming, activating cocatalyst comprises a compound which is a salt of a carbenium ion and a noncoordinating, compatible anion represented by the formula:

$$©^+A^-$$

wherein:

$©^+$ is a $C_{1-20}$ carbenium ion; and $A^-$ is as previously defined. A preferred carbenium ion is the trityl cation, i.e. triphenylmethylium.

A further suitable ion forming, activating cocatalyst comprises a compound which is a salt of a silyliumion and a noncoordinating, compatible anion represented by the formula:

$$R_3Si(X')_q{}^+A^-$$

wherein:

R is $C_{1-0}$ hydrocarbyl, and X', q and $A^-$ are as previously defined.

Preferred silylium salt activating cocatalysts are trimethylsilylium tetrakispentafluorophenylborate, triethylsilylium tetrakispentafluorophenylborate and ether substituted adducts thereof. Silylium salts have been previously generically disclosed in J. Chem Soc. Chem. Comm., 1993, 383–384, as well as Lambert, J. B., et al., Organometallics, 1994, 13, 2430–2443. The use of the above silylium salts as activating cocatalysts for addition polymerization catalysts is disclosed in U.S. Ser. No. 304,314, filed Sep. 12, 1994, published in equivalent form as WO96/08519 on Mar. 21, 1996, the teachings of which are herein incorporated by reference.

Certain complexes of alcohols, mercaptans, silanols, and oximes with tris(pentafluorophenyl)borane are also effective catalyst activators and may be used according to the present invention. Such cocatalysts are disclosed in U.S. Pat. No. 5,296,433, the teachings of which are herein incorporated by reference.

The technique of bulk electrolysis involves the electrochemical oxidation of the metal complex under electrolysis conditions in the presence of a supporting electrolyte comprising a noncoordinating, inert anion. In the technique, solvents, supporting electrolytes and electrolytic potentials for the electrolysis are used such that electrolysis byproducts that would render the metal complex catalytically inactive are not substantially formed during the reaction. More particularly, suitable solvents are materials that are: liquids under the conditions of the electrolysis (generally temperatures from 0 to 100° C.), capable of dissolving the supporting electrolyte, and inert. "Inert solvents" are those that are not reduced or oxidized under the reaction conditions employed for the electrolysis. It is generally possible in view of the desired electrolysis reaction to choose a solvent and a supporting electrolyte that are unaffected by the electrical potential used for the desired electrolysis. Preferred solvents include difluorobenzene (all isomers), dimethoxyethane (DME), and mixtures thereof.

The electrolysis may be conducted in a standard electrolytic cell containing an anode and cathode (also referred to as the working electrode and counter electrode respectively). Suitable materials of construction for the cell are glass, plastic, ceramic and glass coated metal. The electrodes are prepared from inert conductive materials, by which are meant conductive materials that are unaffected by the reaction mixture or reaction conditions. Platinum or palladium are preferred inert conductive materials. Normally an ion permeable membrane such as a fine glass frit separates the cell into separate compartments, the working electrode compartment and counter electrode compartment. The working electrode is immersed in a reaction medium comprising the metal complex to be activated, solvent, supporting electrolyte, and any other materials desired for moderating the electrolysis or stabilizing the resulting complex. The counter electrode is immersed in a mixture of the solvent and supporting electrolyte. The desired voltage may be determined by theoretical calculations or experimentally by sweeping the cell using a reference electrode such as a silver electrode immersed in the cell electrolyte. The background cell current, the current draw in the absence of the desired electrolysis, is also determined. The electrolysis is completed when the current drops from the desired level to the background level. In this manner, complete conversion of the initial metal complex can be easily detected.

Suitable supporting electrolytes are salts comprising a cation and a compatible, noncoordinating anion, $A^-$. Preferred supporting electrolytes are salts corresponding to the formula $G^+A^-$; wherein:

$G^+$ is a cation which is nonreactive towards the starting and resulting complex, and $A^-$ is as previously defined.

Examples of cations, $G^+$, include tetrahydrocarbyl substituted ammonium or phosphonium cations having up to 40 nonhydrogen atoms. Preferred cations are the tetra(n-butylammonuim)- and tetraethylammonium- cations.

During activation of the complexes of the present invention by bulk electrolysis the cation of the supporting electrolyte passes to the counter electrode and $A-$ migrates to the working electrode to become the anion of the resulting oxidized product. Either the solvent or the cation of the supporting electrolyte is reduced at the counter electrode in equal molar quantity with the amount of oxidized metal complex formed at the working electrode. Preferred supporting electrolytes are tetrahydrocarbylammonium salts of tetrakis(perfluoroaryl) borates having from 1 to 10 carbons in each hydrocarbyl or perfluoroaryl group, especially tetra (n-butylammonium)tetrakis(pentafluorophenyl) borate.

A further recently discovered electrochemical technique for generation of activating cocatalysts is the electrolysis of a disilane compound in the presence of a source of a noncoordinating compatible anion. This technique is more fully disclosed and claimed in the previously mentioned U.S. patent application Ser. No. 304,314, published in eqauivalent form as WO 96/08519.

The foregoing electrochemical activating technique and activating cocatalysts may also be used in combination. An especially preferred combination is a mixture of a tri (hydrocarbyl)aluminum or tri(hydrocarbyl)borane compound having from 1 to 4 carbons in each hydrocarbyl group with an oligomeric or polymeric alumoxane compound.

The molar ratio of catalyst/cocatalyst employed preferably ranges from 1:10,000 to 100:1, more preferably from 1:5000 to 10:1, most preferably from 1:1000 to 1:1. Alumoxane, when used by itself as an activating cocatalyst, is employed in large quantity, generally at least 100 times the quantity of metal complex on a molar basis. Tris (pentafluorophenyl)borane, where used as an activating cocatalyst is employed in a molar ratio to the metal complex of form 0.5:1 to 10:1, more preferably from 1:1 to 6:1 most preferably from 1:1 to 5:1. The remaining activating cocatalysts are generally employed in approximately equimolar quantity with the metal complex.

The catalysts, whether or not supported in any of the foregoing methods, may be used to polymerize ethylenically and/or acetylenically unsaturated monomers having from 2 to 100,000 carbon atoms either alone or in combination. Preferred monomers include the $C_{2-20}$ α-olefins especially ethylene, propylene, isobutylene, 1-butene, 1-pentene, 1-hexene, 3-methyl-1-pentene, 4-methyl-1-pentene, 1-octene, 1-decene, long chain macromolecular (α-olefins, and mixtures thereof. Other preferred monomers include styrene, $C_{1-4}$ alkyl substituted styrene, tetrafluoroethylene, vinylbenzocyclobutane, ethylidenenorbornene, 1,4-hexadiene, 1,7-octadiene, vinylcyclohexane, 4-vinylcyclohexene, divinylbenzene, and mixtures thereof with ethylene. Long chain macromolecular α-olefins are vinyl terminated polymeric remnants formed in situ during continuous solution polymerization reactions. Under suitable processing conditions such long chain macromolecular units are readily polymerized into the polymer product along with ethylene and other short chain olefin monomers to give small quantities of long chain branching in the resulting polymer.

Preferred monomers include a combination of ethylene and one or more comonomers selected from monovinyl aromatic monomers, 4-vinylcyclohexene, vinylcyclohexane, norbornadiene, ethylidene-norbornene, $C_{3-10}$ aliphatic α-olefins (especially propylene, isobutylene, 1-butene, 1-hexene, 3-methyl-1-pentene, 4-methyl-1-pentene, and 1-octene), and $C_{4-40}$ dienes. Most preferred monomers are mixtures of ethylene and styrene; mixtures of ethylene, propylene and styrene; mixtures of ethylene, styrene and a nonconjugated diene, especially ethylidenenorbornene or 1,4-hexadiene, and mixtures of ethylene, propylene and a nonconjugated diene, especially ethylidenenorbornene or 1,4-hexadiene.

In general, the polymerization may be accomplished at conditions well known in the prior art for Ziegler-Natta or Kaminsky-Sinn type polymerization reactions, that is, temperatures from 0–250° C., preferably 30 to 200° C. and pressures from atmospheric to 10,000 atmospheres. Suspension, solution, slurry, gas phase, solid state powder polymerization or other process condition may be employed if desired. A support, especially silica, alumina, or a polymer (especially poly(tetrafluoroethylene) or a polyolefin) may be employed, and desirably is employed when the catalysts are used in a gas phase polymerization process. The support is preferably employed in an amount to provide a weight ratio of catalyst (based on metal):support from 1:100,000 to 1:10, more preferably from 1:50,000 to 1:20, and most preferably from 1:10,000 to 1:30.

In most polymerization reactions the molar ratio of catalyst:polymerizable compounds employed is from $10^{-12}$:1 to $10^{-1}$:1, more preferably from $10^{-9}$:1 to $10^{-5}$:1.

Suitable solvents use for solution polymerization are inert liquids. Examples include straight and branched-chain hydrocarbons such as isobutane, butane, pentane, hexane, heptane, octane, and mixtures thereof; cyclic and alicyclic hydrocarbons such as cyclohexane, cycloheptane, methylcyclohexane, methylcycloheptane, and mixtures thereof; perfluorinated hydrocarbons such as perfluorinated $C_{4-10}$ alkanes, and alkyl-substituted aromatic compounds such as benzene, toluene, xylene, and ethylbenzene. Suitable solvents also include liquid olefins which may act as monomers or comonomers.

The catalysts may be utilized in combination with at least one additional homogeneous or heterogeneous polymerization catalyst in the same reactor or in separate reactors connected in series or in parallel to prepare polymer blends having desirable properties. An example of such a process is disclosed in WO 94/00500, equivalent to U.S. Ser. No. 07/904,770, as well as U.S. Ser. No. 08/10958, filed Jan. 29, 1993, the teachings or which are hereby incorporated by reference herein.

Utilizing the present catalysts, a-olefin homopolymers and copolymers having densities from 0.85 g/cm$^3$ to 0.96 g/cm$^3$, and melt flow rates from 0.001 to 1000.0 dg/min are readily attained in a highly efficient process.

The catalysts of the present invention are particularly advantageous for the production of ethylene homopolymers and ethylenela-olefin copolymers having high levels of long chain branching. The use of the catalysts of the present invention in continuous polymerization processes, especially continuous, solution polymerization processes, allows for elevated reactor temperatures which favor the formation of vinyl terminated polymer chains that may be incorporated into a growing polymer, thereby giving a long chain branch. The use of the present catalyst compositions advantageously allows for the economical production of ethylene/α-olefin copolymers having processability similar to high pressure, free radical produced low density polyethylene.

The present catalyst compositions may be advantageously employed to prepare olefin polymers having improved processing properties by polymerizing ethylene alone or ethylene/α-olefin mixtures with low levels of a "H" branch inducing diene, such as norbornadiene, 1,7-octadiene, or 1,9-decadiene. The unique combination of elevated reactor temperatures, high molecular weight (or low melt indices) at high reactor temperatures and high comonomer reactivity advantageously allows for the economical production of polymers having excellent physical properties and processability. Preferably such polymers comprise ethylene, a $C_{3-20}$ α-olefin and a "H"-branching comonomer. Preferably, such polymers are produced in a solution process, most preferably a continuous solution process.

The catalyst composition may be prepared as a homogeneous catalyst by addition of the requisite components to a solvent in which polymerization will be carried out by solution polymerization procedures. The catalyst composition may also be prepared and employed as a heterogeneous catalyst by adsorbing the requisite components on an inert inorganic or organic particulated solid. Examples of such solids include, silica, silica gel, alumina, trialkylaluminum compounds, and organic or inorganic polymeric materials, especially polyolefins. In an preferred embodiment, a heterogeneous catalyst is prepared by co-precipitating the metal complex, an inert, inorganic compound and an activator, especially an ammonium salt of a hydroxyaryl (trispentafluorophenyl)borate, such as an ammonium salt of (4-hydroxy-3,5-ditertiarybutylphenyl) (trispentafluorophenylborate. A preferred inert, inorganic compound for use in this embodiment is a tri ($C_{1-4}$ alkyl) aluminum compound.

When prepared in heterogeneous or supported form, the catalyst composition is employed in a slurry or gas phase polymerization. As a practical limitation, slurry polymerization takes place in liquid diluents in which the polymer product is substantially insoluble. Preferably, the diluent for slurry polymerization is one or more hydrocarbons with less than 5 carbon atoms. If desired, saturated hydrocarbons such as ethane, propane or butane may be used in whole or part as the diluent. Likewise the a-olefin monomer or a mixture of different a-olefin monomers may be used in whole or part as the diluent. Most preferably at least a major part of the diluent comprises the α-olefin monomer or monomers to be polymerized.

At all times, the individual ingredients as well as the recovered catalyst components must be protected from oxygen and moisture. Therefore, the catalyst components and catalysts must be prepared and recovered in an oxygen and moisture free atmosphere. Preferably, therefore, the reactions are performed in the presence of an dry, inert gas such as, for example, nitrogen.

The polymerization may be carried out as a batchwise or a continuous polymerization process A continuous process is preferred, in which event catalyst, ethylene, comonomer, and optionally solvent are continuously supplied to the reaction zone and polymer product continuously removed therefrom.

Without limiting in any way the scope of the invention, one means for carrying out such a polymerization process is as follows: In a stirred-tank reactor, the monomers to be polymerized are introduced continuously together with solvent and an optional chain transfer agent. The reactor contains a liquid phase composed substantially of monomers together with any solvent or additional diluent and dissolved polymer. If desired, a small amount of a "H"-branch inducing diene such as norbornadiene, 1,7-octadiene or 1,9- decadiene may also be added. Catalyst and cocatalyst are continuously introduced in the reactor liquid phase. The reactor temperature and pressure may be controlled by adjusting the solvent/monomer ratio, the catalyst addition rate, as well as by cooling or heating coils, jackets or both. The polymerization rate is controlled by the rate of catalyst addition. The ethylene content of the polymer product is determined by the ratio of ethylene to comonomer in the reactor, which is controlled by manipulating the respective feed rates of these components to the reactor. The polymer product molecular weight is controlled, optionally, by controlling other polymerization variables such as the temperature, monomer concentration, or by the previously mention chain transfer agent, such as a stream of hydrogen introduced to the reactor, as is well known in the art. The reactor effluent is contacted with a catalyst kill agent such as water. The polymer solution is optionally heated, and the polymer product is recovered by flashing off gaseous monomers as well as residual solvent or diluent at reduced pressure, and, if necessary, conducting further devolatilization in equipment such as a devolatilizing extruder. In a continuous process the mean residence time of the catalyst and polymer in the reactor generally is from about 5 minutes to 8 hours, and preferably from 10 minutes to 6 hours. By using a catalyst that incorporates large amounts of hindered monovinyl monomer, hindered monovinyl homopolymer formed from residual quantities of the monomer are substantially reduced.

The process of the present invention can be employed to advantage in the gas phase copolymerization of olefins. Gas phase processes for the polymerization of olefins, especially the homopolymerization and copolymerization of ethylene and propylene, and the copolymerization of ethylene with higher a-olefins such as, for example, 1-butene, 1-hexene, 4-methyl-1-pentene are well known in the art. In such processes, cooling of the reactor may be provided by the use of recycle gas, which is fed as a volatile liquid to the bed to provide an evaporative cooling effect. The volatile liquid employed in this case can be, for example, a volatile inert liquid, for example, a saturated hydrocarbon having about 3 to about 8, preferably 4 to 6, carbon atoms. In the case that the monomer or comonomer itself is a volatile liquid (or can be condensed to provide such a liquid) this can be fed to the bed to provide an evaporative cooling effect. Examples of olefin monomers which can be employed in this manner are olefins containing about three to about eight, preferably three to six carbon atoms. The volatile liquid evaporates in the hot fluidized bed to form gas which mixes with the fluidizing gas. If the volatile liquid is a monomer or comonomer, it will undergo some polymerization in the bed. The evaporated liquid then emerges from the reactor as part of the hot recycle gas, and enters the compression/heat exchange part of the recycle loop. The recycle gas is cooled in the heat exchanger and, if the temperature to which the gas is cooled is below the dew point, liquid will condense from the gas. This liquid is desirably recycled continuously to the fluidized bed. It is possible to recycle the condensed liquid to the bed as liquid droplets carried in the recycle gas stream. This type of process is described, for example in EP 89691; U.S. Pat. No. 4,543,399; WO 94/25495 and U.S. Pat. No. 5,352,749, which are hereby incorporated by reference. A particularly preferred method of recycling the liquid to the bed is to separate the liquid from the recycle gas stream and to reinject this liquid directly into the bed, preferably using a method which generates fine droplets of the liquid within the bed. This type of process is described in BP Chemicals' WO 94/28032, which is hereby incorporated by reference.

The polymerization reaction occurring in the gas fluidized bed is catalyzed by the continuous or semi-continuous addition of catalyst. Such catalyst can be supported on an inorganic or organic support material as described above.

The polymer is produced directly in the fluidized bed by catalyzed copolymerization of the monomer and one or more comonomers on the fluidized particles of catalyst, supported catalyst or prepolymer within the bed. Start-up of the polymerization reaction is achieved using a bed of preformed polymer particles, which are preferably similar to the target polyolefin, and conditioning the bed according to techniques that are well known in the art. Such processes are used commercially on a large scale for the manufacture of high density polyethylene (HDPE), medium density polyethylene (MDPE), linear low density polyethylene (LLDPE) and polypropylene.

The gas phase process employed can be, for example, of the type which employs a mechanically stirred bed or a gas fluidized bed as the polymerization reaction zone. Preferred is the process wherein the polymerization reaction is carried out in a vertical cylindrical polymerization reactor containing a fluidized bed of polymer particles supported above a perforated plate, the fluidization grid, by a flow of fluidization gas.

The gas employed to fluidize the bed comprises the monomer or monomers to be polymerized, and also serves as a heat exchange medium to remove the heat of reaction from the bed. The hot gases emerge from the top of the reactor, normally via a tranquilization zone, also known as a velocity reduction zone, having a larger cross-sectional area than the fluidized bed and wherein fine particles entrained in the gas stream have an opportunity to gravitate back into the bed. It can also be advantageous to use a cyclone to remove ultra-fine particles from the hot gas stream. The gas is then normally recycled to the bed by means of a blower or compressor and one or more heat exchangers to strip the gas of the heat of polymerization. The produced polymer is discharged continuously or discontinuously from the fluidized bed as desired.

The gas phase processes suitable for the practice of this invention are preferably continuous processes which provide for the continuous supply of reactants to the reaction zone of the reactor and the removal of products from the reaction zone of the reactor, thereby providing a steady-state environment on the macro scale in the reaction zone of the reactor.

Typically, the fluidized bed of the gas phase process is operated at temperatures greater than 50° C., preferably from about 60° C. to about 110° C., more preferably from about 70° C. to about 110° C.

Typically the molar ratio of comonomer to monomer used in the polymerization depends upon the desired density for the composition being produced and is about 0.5 or less. Desirably, when producing materials with a density range of from about 0.91 to about 0.93 the comonomer to monomer ratio is less than 0.2, preferably less than 0.05, even more preferably less than 0.02, and may even be less than 0.01. Typically, the ratio of hydrogen to monomer is less than about 0.5, preferably less than 0.2, more preferably less than 0.05, even more preferably less than 0.02 and may even be less than 0.01.

The above-described ranges of process variables are appropriate for the gas phase process of this invention and may be suitable for other processes adaptable to the practice of this invention.

A number of patents and patent applications describe gas phase processes which are adaptable for use in the process of this invention, particularly, U.S. Pat. Nos. 4,588,790; 4,543,399; 5,352,749; 5,436,304; 5,405,922; 5,462,999; 5,461,123; 5,453,471; 5,032,562; 5,028,670; 5,473,028; 5,106,804; 5,541,270 and EP applications 659,773; 692,500; and PCT Applications WO 94/29032, WO 94/25497, WO 94/25495, WO 94/28032; WO 95/13305; WO 94/26793; and WO 95/07942 the teachings of all of which are hereby incorporated herein by reference.

EXAMPLES

The skilled artisan will appreciate that the invention disclosed herein may be practiced in the absence of any component which has not been specifically disclosed. The following examples are provided as further illustration of the invention and are not to be construed as limiting. Unless stated to the contrary all parts and percentages are expressed on a weight basis.

$^1$H and $^{13}$C NMR spectra recorded on a Varian XL (300 MHz) spectrometer were used to identify all products. Crystal structures of two structures were also obtained. Tetrahydrofuran (THF), diethylether, toluene, and hexane were used following passage through double columns charged with activated alumina and copper/manganese mixed metal oxide catalyst (available from Engelhard Corp.). The compounds n-BuLi, dimethyldichlorosilane, and indan were all used as purchased from Aldrich Chemical Company. All syntheses were performed under dry nitrogen atmosphere using a combination of glove box and high vacuum techniques.

Example 1

Synthesis of: dichloro[N-(1,1-dimethylethyl)-1,1-dimethyl-[1,2,3,4,5-η)-1,5,6,7-tetrahydro-2-methyl-s-indacen-1-yl]silanaminto(2-)-N]titanium (also referred to as dimethylsilyl(2-methyl-s-indacenyl)(t-butylamido)Titaniumdichloride

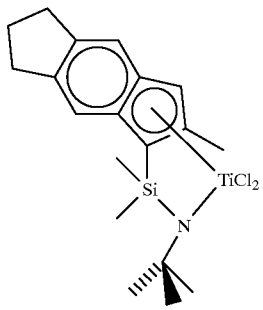

1a) Preparation of 5,6,7-tetrahydro-2-methyl-s-indacen-1-one

Indan (59.0876 g, 0.5000 moles) and 2-bromoisobutyryl bromide (114.9493 g, 0.5000 moles) were stirred in CH$_2$Cl$_2$ (500 mL) at 0° C. as AlC3 (201.36 g, 1.5101 moles) was added slowly as a solid under a nitrogen flow. This mixture was then allowed to stir for 6 hours at 20–25° C. After the reaction period the mixture was poured over ice and allowed to sit 16 hours. The mixture was then decanted into a separatory funnel and the remaining salts washed well with CH$_2$Cl$_2$. The organic layer was then separated and the volatiles removed resulting in the isolation of a dark oil. Vacuum distillation resulted in the isolation of the desired product as a yellow oil (82.43 g, 88.5 percent).

1b) Preparation of s-Indacen-1,2,3,5-tetrahydro-6-methyl 5,6,7-tetrahydro-2-methyl-s-indacen-1-one (40.00 g, 0.2148 moles) was stirred in diethylether (150 mL) at 0° C. under nitrogen as NaBH$_4$ (8.12 g, 0.2148 moles) as EtOH (100 mL) was added slowly. The mixture was then allowed to stir 16 hours at 20–25° C. After the reaction period the mixture was poured on ice and the mixture acidified using aqueous 1 M HCl solution. The organic fraction was then washed with 1 M HI. (2×100 mL). The volatiles were then removed from the solution and the residue redissolved in benzene and refluxed with p-toluensulphonic acid (0.11 g) using a Dean-Stark apparatus for 5 hours. The mixture was then extracted using 1 M NaHCO$_3$ (2×100 mL). The organic layer was separated and the volatiles removed resulting in the isolation of the desired product as a white crystalline solid (28.36 g, 77.6 percent).

1c) Preparation of (1,5,6,7-tetrahydro-2-methyl-s-indacen-1-yl) lithium s-indacen-1,2,3,5-tetrahydro-6-methyl (25.000 g, 0.14684 moles) was stirred in hexane (400 mL) as nBuLi (0.17621 moles, 70.48 mL of 2.5 M solution in hexane) was added slowly. This mixture was then allowed to stir 16 hours during which time a solid precipitated. After the reaction period the mixture was filtered resulting in the isolation of the desired product as a pale yellow solid which was used without further purification or analysis (24.3690 g, 94.2 percent).

1d) Preparation of N-(1,1-dimethylethyl)-1,1-dimethyl-1-(1,5,6,7-tetrahydro-2-methyl-s-indacen-1-yl)silanamine (1,5,6,7-tetrahydro-2-methyl-s-indacen-1-yl) lithium (25.0 g, 0.1419 moles) in THF (200 mL) was added dropwise to a solution of dimethylsilyl(t-butylamino)chloride (23.518 g, 0.1419 moles) in THF (250 mL) over a 1 hour period of time. This mixture was then allowed to stir for 20 hours. After the reaction period the volatiles were removed and the residue extracted and filtered using hexane. Removal of the hexane resulted in the isolation of the desired product as a red-yellow oil (37.55 g, 88.0 percent).

1e) Preparation of dilithio N-(1,1-dimethylethyl)-1,1-dimethyl-1-(1,5,6,7-tetrahydro-2-methyl-s-indacen-1-yl)silanamide N-(1,1-dimethylethyl)-1,1-dimethyl-1-(1,5,6,7-tetrahydro-2-methyl-s-indacen-1-yl)silanamine (8.00 g, 0.2671 moles) was stirred in hexane (110 mL) as nBuLi (0.05876 moles, 23.5 mL of 2.5 M solution in hexane) was added dropwise. This mixture was then allowed to stir 16 hours. After the reaction period the desired product was isolated as a light yellow solid via filtration which was used without further purification or analysis (6.22 g, 75 percent).

1f) Preparation of dichloro[N-(1,1-dimethylethyl)-1,1-dimethyl-[1,2,3,4,5-η)-1,5,6,7-tetrahydro-2-methyl-s-indacen-1-yl]silanaminto(2-)-N]titanium Dilithio N-(1,1-dimethylethyl)-1,1-dimethyl-1-(1,5,6,7-tetrahydro-2-methyl-s-indacen-1-yl)silanamide (4.504 g, 0.01446 moles) in THF (40 mL) was added dropwise to a slurry of TiCl$_3$(THF)$_3$ (5.359 g, 0.001446 moles) in THF (100 mL). This mixture was allowed to stir for 1 hour. PbCl$_2$ (2.614 g, 0.000940 moles) was then added and the mixture allowed to stir for an additional hour. After the reaction period the volatiles were removed and the residue extracted and filtered using toluene. Removal of the toluene resulted in the isolation of a dark residue. This residue was then slurried in hexane and the desired product was then isolated via filtration as a red solid (3.935 g, 65.0 percent). FIG. 1 is the X-ray crystal structure of this complex.

Example 2

Synthesis of: dimethyl[N-(1,1-dimethylethyl)-1,1-dimethyl-[1,2,3,4,5-η)-1,5,6,7-tetrahydro-2-methyl-s-indacen-1-yl]silanaminto(2-)-N]titanium (also referred to as dimethylsilyl(2-methyl-s-indacenyl)(t-butylamido)Titaniumdimethyl Dichloro[N-(1,1-dimethylethyl)-1,1-dimethyl-[1,2,3,4,5-η)-1,5,6,7-tetrahydro-2-methyl-s-indacen-1-yl]silanaminto (2-)-N] titanium (1f)) (0.450 g, 0.00108 moles) was stirred in diethylether (30 mL) as MeMgBr (0.00324 moles, 1.08 mL of 3.0 M solution in diethylether) was added slowly. This mixture was then stirred for 30 minutes. After the reaction period the volatiles were removed and the residue extracted and filtered using hexane. Removal of the hexane resulted in the isolation of the desired product as a solid (0.368 g, 90.6 percent).

Example 3

Synthesis of: dichloro[N-(cyclohexyl)-1,1-dimethyl-[1,2,3,4,5-η)-1,5,6,7-tetrahydro-2-methyl-s-indacen-1-yl]silanaminto(2-)-N]titanium (also referred to as dimethylsilyl(2-methyl-s-indacenyl)(cyclohexyl-amido)Titaniumdichloride

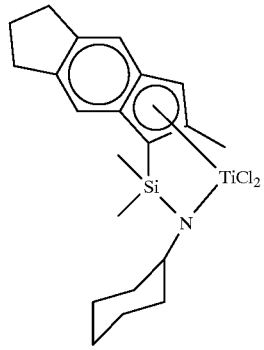

3a) Preparation of chlorodimethyl(1,5,6,7-tetrahydro-2-methyl-s-indacen-1-yl)silane 1,5,6,7-tetrahydro-2-methyl-s-indacen-1-yl)lithium (1 c)) (24.369 g, 0.13831 moles) in THF (100 mL) was added dropwise to a solution of $Me_2SiCl_2$ (89.252 g, 0.69155 moles) in THF (150 mL). This mixture was then allowed to stir at 20–25° C. for 5 hours. After the reaction period the volatiles were removed and the residue extracted and filtered using hexane. The removal of the hexane resulted in the isolation of the desired product as an off-white crystalline solid (31.1451 g, 85.7 percent).

3b) Preparation of N-(cyclohexyl)-1,1-dimethyl-1-(1,5,6,7-tetrahydro-2-methyl-s-indacen-1-yl)silanamine Chlorodimethyl(1,5,6,7-tetrahydro-2-methyl-s-indacen-1-yl) silane (5.67 g, 0.0216 moles) was stirred in hexane (50 mL) as $NEt_3$ (2.18 g, 0.0216 moles) and cyclohexylamine (2.13 g, 0.0216 moles) were added. This mixture was allowed to stir 16 hours. After the reaction period the mixture was filtered and the volatiles removed resulting in the isolation of the desired product as a yellow oil (6.62 g, 94.3 percent).

3c) Preparation of [N-(cyclohexyl)-1,1-dimethyl-[1,2,3,4,5-η)-1,5,6,7-tetrahydro-2-methyl-s-indacen-1-yl]silanaminto(2-)-N]dilithium N-(cyclohexyl)-1,1-dimethyl-1-(1,5,6,7-tetrahydro-2-methyl-s-indacen-1-yl)silanamine (6.67 g, 0.02048 moles) was stirred in hexane (100 mL) as nBuLi (0.04302 moles, 21.51 mL of 2.0 M solution in cyclohexane) was added slowly. This mixture was then allowed to stir 16 hours. After the reaction period the desired product was isolated as a solid which was used without further purification or analysis (7.23 g, product still contained residual hexane).

3d) Preparation of dichloro[N-(cyclohexyl)-1,1-dimethyl-[1,2,3,4,5-η)-1,5,6,7-tetrahydro-2-methyl-s-indacen-1-yl]silanaminto(2-)-N]titanium

[N-(cyclohexyl)-1,1-dimethyl-[1,2,3,4,5-η)-1,5,6,7-tetrahydro-2-methyl-s-indacen-1-yl]silanaminto(2-)-N] dilithium (7.23 g, 0.0214 moles) was slowly added as a solid to a slurry of $TiCl_3(THF)_3$ (7.93 g, 0.0214 moles) in THF (50 mL). This mixture was allowed to stir for 30 minutes. $PbCl_2$ (3.80 g, 0.0136 moles) was then added and the mixture allowed to stir for an additional hour. After the reaction period the volatiles were removed and the residue extracted and filtered using toluene. Removal of the toluene resulted in the isolation of a dark residue. This residue was then slurried in hexane and the desired product isolated via filtration as a solid (3.71 g, 39.2 percent).

Example 4

Synthesis of: dimethyl[N-(cyclohexyl)-1,1-dimethyl-[1,2,3,4,5-η)-1,5,6,7-tetrahydro-2-methyl-s-indacen-1-yl]silanaminto(2-)-N]titanium (also referred to as dimethylsilyl(2-methyl-s-indacenyl)(cyclohexyl-amido)Titaniumdimethyl Dichloro[N-(cyclohexyl)-1,1-dimethyl-[1,2,3,4,5-η)-1,5,6,7-tetrahydro-2-methyl-s-indacen-1-yl]silanaminto(2-)-N] titanium (0.400 g, 0.00904 moles) was stirred in diethylether (50 mL) as MeMgBr (0.0181 moles, 0.60 mL of 3.0 M solution in diethylether) was added slowly. This mixture was then stirred for 1 hour. After the reaction period the volatiles were removed and the residue extracted and filtered using hexane. Removal of the hexane resulted in the isolation of the desired product as a solid (0.309 g, 85.1 percent).

Example 5

Synthesis of: dichloro[N-(1,1-dimethylethyl)-1,1-dimethyl-[1,2,3,4,5-η)-1,5,6,7-tetrahydro-2,3-dimethyl-s-indacen-1-yl ]silanaminto(2-)-N]titanium (also referred to as dimethylsilyl(2,3-dimethyl-s-indacenyl)(t-butylamido)Titaniumdichloride

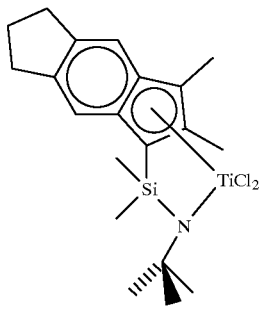

5a) Preparation of s-Indacen-1,2,3,5-tetrahydro-6,7-dimethyl

-s-indacen-1,2,3,5-tetrahydro-6-methyl (36.0647 g, 0.2118 moles) was stirred in hexane as nBuLi (0.230 moles, 115.0 mL of 2.0 M solution in cyclohexane) was added. This mixture was then allowed to stir 16 hours. After the reaction period the volatiles were removed and the white solid redissolved in THF (100 mL) and added dropwise to a mixture of MeI (51.3673 g, 0.3619 moles) in THF (75 mL) at 0 ° C. This mixture was then allowed to stir 16 hours at 20–25° C. The volatiles were then removed and the residue extracted and filtered using hexane. Removal of the hexane resulted in the isolation of the desired product as a pale yellow oil (36.8503 g, 94.4 percent).

5b) Preparation of (1,5,6,7-tetrahydro-2,3-dimethyl-s-indacen-1-yl)lithium s-Indacen-1,2,3,5-tetrahydro-6,7-dimethyl (15.00 g, 0.08140 moles) was stirred in hexane (100 mL) as nBuLi (0.0895 moles, 35.800 mL of 2.5 M solution in hexane) was slowly added. This mixture was then allowed to stir 16 hours. After the reaction period the solid was collected via suction filtration as an light tan powder which was used without further purification or analysis (9.27 g, 60.0 percent).

5c) Preparation of chlorodimethyl(1,5,6,7-tetrahydro-2,3-dimethyl-s-indacen-1-yl)silane (1,5,6,7-tetrahydro-2,3-dimethyl-s-indacen-1-yl)lithium (9.27 g, 0.04874 moles) in THF (90 mL) was added dropwise to a solution of $Me_2SiCl_2$ (18.90 g, 0.1463 moles) in THF (50 mL). This mixture was then allowed to stir at 20–25 ° C. 16 hours. After the reaction period the volatiles were removed and the residue extracted and filtered using hexane. The removal of the hexane resulted in the isolation of the desired product as an orange/brown oil (10.35 g, 76.7 percent).

5d) Preparation of N-(1,1-dimethylethyl)-1,1-dimethyl-1-(1,5,6,7-tetrahydro-2,3-dimethyl-s-indacen-1-yl) silanamine Chlorodimethyl(1,5,6,7-tetrahydro-2,3-dimethyl-s-indacen-1-yl) silane (3.537 g, 0.01217 moles) was stirred in hexane (50 mL) as $NEt_3$ (1.94 g, 0.01916 moles) and t-butylamine (1.12 g, 0.01533 moles) were added. This mixture was allowed to stir 16 hours. After the reaction period the mixture was filtered and the volatiles removed resulting in the isolation of the desired product as a light yellow oil (3.537 g, 88.6 percent).

5e) Preparation of [N-(1,1-dimethylethyl)-1,1-dimethyl-[1,2,3,4,5-η)-1,5,6,7-tetrahydro-2,3-dimethyl-s-indacen-1-yl]silanaminto(2-)-N dilithium N-(1,1-dimethylethyl)-1,1-dimethyl-1-(1,5,6,7-tetrahydro-2,3-dimethyl-s-indacen-1-yl)silanamine (3.461 g, 0.01107 moles) was stirred in hexane (100 mL) as nBuLi (0.02325 moles, 14.5 mL of 1.6 M solution in hexane) was added slowly. This mixture was then allowed to stir 16 hours. After the reaction period the volatiles were removed and the desired product was isolated as an orange glassy solid which was used without further purification or analysis (3.853 g, product still contained hexane).

5f) Preparation of dichloro[N-(1,1-dimethylethyl)-1,1-dimethyl-[1,2,3,4,5-.eta.)-1,5,6,7-tetrahydro-2,3-dimethyl-3-s-indacen-1-yl]silanaminto(2-)-N] titanium

[N-(1,1-dimethylethyl)-1,1-dimethyl-l1,2,3,4,5-yl)-1,5,6,7-tetrahydro-2,3-dimethyl-s-indacen-1-yl]silanaminto(2-)-N dilithium (0.500 g, 0.01536 moles) was slowly added as a solid to a slurry of $TiCl3(THF)_3$ (0.455 g, 0.001229 moles) in THF (50 mL). This mixture was allowed to stir for 2 hours. $PbCl_2$ (0.205 g, 0.0007374 moles) was then added and the mixture allowed to stir for an additional hour. After the reaction period the volatiles were removed and the residue extracted and filtered using toluene. Removal of the toluene resulted in the isolation of a dark residue. This residue was then slurried in hexane and cooled in a refrigerator for 72 hours. The desired product was then isolated via filtration as a solid (0.196 g, 49.1 percent).

Example 6

Synthesis of: dimethyl[N-(1,1-dimethylethyl)-1,1-dimethyl-[1,2,3,4,5-η)-1,5,6,7-tetrahydro-2,3-dimethyl-s-indacen-1-yl]silanaminto(2-)-N]titanium (also referred to as dimethylsilyl(2,3-dimethyl-s-indacenyl)(t-butylamido)Titaniumdimethyl Dichloro[N-(1,1-dimethylethyl)-1,1-dimethyl-[1,2,3,4,5-.eta.)-1,5,6,7-tetrahydro-2,3-dimethyl-s-indacen-1-yl] silanaminto(2-)-N] titanium (0.433 g, 0.001006 moles) was stirred in diethylether (50 mL) as MeMgBr (0.002012 moles, 0.67 mL of 3.0 M solution in diethylether) was added slowly. This mixture was then stirred for 1 hour. After the reaction period the volatiles were removed and the residue extracted and filtered using hexane. Removal of the hexane resulted in the isolation of the desired product as an orange-red solid (0.347 g, 88.5 percent).

Example 7

Synthesis of: dichloro[N-(cyclohexyl)-1,1-dimethyl-[1,2,3,4,5-η)-1,5,6,7-tetrahydro-2,3-dimethyl-s-indacen-1-yl]silanaminto(2-)-N]titanium (also referred to as dimethylsilyl(2,3-dimethyl-s-indacenyl)(cyclohexylamido)Titaniumdichloride

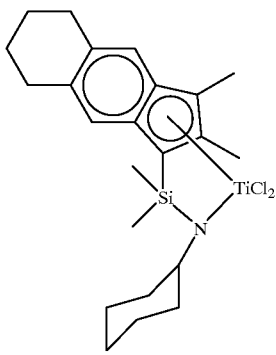

7a) Preparation of N-(cyclohexyl)-1,1-dimethyl-1-(1,5,6,7-tetrahydro-2,3-dimethyl-s-indacen-1-yl)silanamine Chlorodimethyl(1,5,6,7-tetrahydro-2,3-dimethyl-s-indacen-1-yl)silane (5.00 g, 0.01806 moles) was stirred in hexane (80 mL) as $NEt_3$ (3.29 g, 0.03251 moles) and t-cyclohexylamine (1.81 g, 0.01824 moles) were added. This mixture was allowed to stir 16 hours. After the reaction period the mixture was filtered and the volatiles removed resulting in the isolation of the desired product as a yellow oil (5.55 g, 90.9 percent).

7b) Preparation of [N-(cyclohexyl)-1,1-dimethyl-[1,2,3,4,5-η)-1,5,6,7-tetrahydro-2,3-dimethyl-s-indacen-1-yl]silanaminto(2-)-N]dilithium N-(cyclohexyl)-1,1-dimethyl-1-(1,5,6,7-tetrahydro-2,3-dimethyl-s-indacen-1-yl)silanamine (5.30 g, 0.01570 moles) was stirred in hexane (75 mL) as n-BuLi (0.03454 moles, 13.8 mL of 2.5 M solution in hexane) was added slowly. This mixture was then allowed to stir for 72 hours. After the reaction period the hexane was decanted away and the volatiles were removed resulting in the isolation of the desired product as an orange glassy solid which was used without further purification or analysis (5.56 g, 99.9 percent).

7c) Preparation of dichloro[N-(cyclohexyl)-1,1-dimethyl-[1,2,3,4,5-η)-1,5,6,7-tetrahydro-2,3-dimethyl-s-indacen-1-yl]silanaminto(2-)-N]titanium

[N-(cyclohexyl)-1,1-dimethyl-[1,2,3,4,5-η)-1,5,6,7-tetrahydro-2,3-dimethyl-s-indacen-1-yl]silanaminto(2-)-N]dilithium (0.500 g, 0.01428 moles) was slowly added as a solid to a slurry of $TiCl_3(THF)_3$ (0.529 g, 0.001428 moles) in THF 50 mL. This mixture was allowed to stir for 2 hours. $PbCl_2$ (0.317 g, 0.001142 moles) was then added and the mixture allowed to stir for an additional hour. After the reaction period the volatiles were removed and the residue extracted and filtered using toluene. Removal of the toluene resulted in the isolation of a dark residue. This residue was then slurried in hexane and cooled in a refrigerator for 72 hours. The desired product was then isolated via filtration as a solid (0.259 g, 43.8 percent).

Example 8

Synthesis of: dimethyl[N-(cyclohexyl)-1,1-dimethyl-[1,2,3,4,5-η)-1,5,6,7-tetrahydro-2,3-dimethyl-s-indacen-1-yl]silanaminto(2-)-N]titanium (also referred to as dimethylsilyl(2,3-dimethyl-s-indacenyl)(cyclohexylamido)Titaniumdimethyl Dichloro[N-(cyclohexyl)-1,1-dimethyl-[1,2,3,4,5-.eta.)-1,5,6,7-tetrahydro-2,3-dimethyl-s-indacen-1-yl]silanaminto (2-)-N] titanium (0.300 g, 0.0006588 moles) was stirred in diethylether (50 mL) as MeMgBr (0.001447 moles, 0.48 mL of 3.0 M solution in diethylether) was added slowly. This mixture was then stirred for 1 hour. After the reaction period the volatiles were removed and the residue extracted and filtered using hexane. Removal of the hexane resulted in the isolation of the desired product as an orange solid (0.249 g, 91.2 percent).

Example 9

Synthesis of: dichloro[N-(1,1-dimethylethyl)-1,1-dimethyl-[1,2,3,4,5-η)-1,5,6,7-tetrahydro-2-methyl-3-s-indacen-1-yl]silanaminto(2-)-N]titanium (also referred to as dimethylsilyl(2-methyl-3-phenyl-s-indacenyl)(t-butylamido)Titaniumdichloride

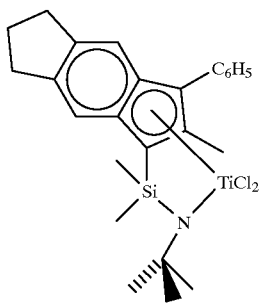

9a) Preparation of s-Indacen-1,2,3,5-tetrahydro-6-methyl-7-phenyl s-Indacen-1,2,3,5-tetrahydro-6-methyl (1b)),(20.00 g, 0.0174 moles) was stirred in diethylether (200 mL) at 0° C. under nitrogen as PhMgBr (0.150 moles, 50.00 mL of 3.0 M solution in diethylether) was added slowly. The mixture was then allowed to stir at 20–25° C. for 3 hours. After the reaction period the mixture was quenched by pouring over ice. The mixture was then acidified (pH=1) with aqueous HCl and stirred vigorously for 30 minutes. The organic layer was then separated and washed with $H_2O$ (2×100 mL) and then dried over $MgSO_4$. Filtration followed by the removal of the volatiles resulted in the isolation of a pale yellow oil. The desired product was isolated as a white solid following the recrystallization of the yellow oil from hexane at 0° C. (18.90 g, 71.4 percent).

9b) Preparation of (6-methyl-7-phenyl-1,2,3,5-tetrahydro-s-indacenyl)lithium s-Indacen-1,2,3,5-tetrahydro-6-methyl-7-phenyl (18.90 g, 0.07672 moles) was stirred in hexane (200 mL) as nBuLi (0.10 moles, 50.00 mL of 2.0 M solution in cyclohexane) was slowly added. This mixture was then allowed to stir 16 hours. After the reaction period the solid was collected via suction filtration as an off-white powder which was used without further purification or analysis (17.8305 g, 92.1 percent).

9c) Preparation of chlorodimethyl(1,5,6,7-tetrahydro-2-methyl-3-phenyl-s-indacen-1-yl)silane (6-Methyl-7-phenyl-1,2,3,5-tetrahydro-s-indacenyl) lithium (17.8305 g, 0.07068 moles) 25 in THF (50 mL) was added dropwise to a solution of Me$_2$SiCl$_2$ (21.3694 g, 0.1656 moles) in THF (100 mL) at 0° C. This mixture was then allowed to stir at 20–25° C. 16 hours. After the reaction period the volatiles were removed and the residue extracted and filtered using hexane. The removal of the hexane resulted in the isolation of the desired product as a viscous yellow oil (23.0231 g, 96.1 percent).

9d) Preparation of N-(1,1-dimethylethyl)-1,1-dimethyl-1-(1,5,6,7-tetrahydro-2-methyl-3-phenyl-s-indacen-1-yl)silanamine Chlorodimethyl(1,5,6,7-tetrahydro-2-methyl-3-phenyl-s-indacen-1-yl)silane (5.3483 g, 0.01578 moles) was stirred in hexane (100 mL) as NEt$_3$ (2.2579 g, 0.02231 moles) and t-butylamine (1.9898 g, 0.02721 moles) were added. This mixture was allowed to stir for 24 hours. After the reaction period the mixture was filtered and the volatiles removed resulting in the isolation of the desired product as a yellow oil (5.4118 g, 91.3 percent).

9e) Preparation of [N-(1,1-dimethylethyl)-1,1-dimethyl-[1,2,3,4,5-η)-1,5,6,7-tetrahydro-2-methyl-3-phenyl-s-indacen-1-yl]silanaminto(2-)-N]dilithium N-(1,1-dimethylethyl)-1,1-dimethyl-1-(1,5,6,7-tetrahydro-2-methyl-3-phenyl-s-indacen-1-yl)silanamine (5.4118 g, 0.01441 moles) was stirred in hexane (100 mL) as nBuLi (0.032 moles, 16.00 mL of 2.0 M solution in cyclohexane) was added slowly. This mixture was then allowed to stir 16 hours. After the reaction period the desired product was isolated as a pale yellow solid via filtration which was used without further purification or analysis (5.2255 g, 93.6 percent).

9f) Preparation of dichloro[N-(1,1-dimethylethyl)-1,1-dimethyl-[1,2,3,4,5-η)-1,5,6,7-tetrahydro-2-methyl-3-phenyl-s-indacen-1-yl]silanaminto(2-)-N]titanium

[N-(1,1-dimethylethyl)-1,1-dimethyl-[1,2,3,4,5-η)-1,5,6,7-tetrahydro-2-methyl-3-phenyl-s-indacen-1-yl]silanaminto(2-)-N]dilithium (5.2255 g, 0.01349 moles) in THF (50 mL) was added dropwise to a slurry of TiCl$_3$(THF)$_3$ (4.9975 g, 0.01349 moles) in THF (100 mL). This mixture was allowed to stir for 2 hours. PbCl$_2$ (1.9286 g, 0.006935 moles) was then added and the mixture allowed to stir for an additional hour. After the reaction period the volatiles were removed and the residue extracted and filtered using toluene. Removal of the toluene resulted in the isolation of a dark residue. This residue was then slurried in hexane and cooled to −10° C. The desired product was then isolated via filtration as a red crystalline solid (2.7804 g, 41.9 percent).

Example 10

Synthesis of: dimethyl[N-(1,1-dimethylethyl)-1,1-dimethyl-[1,2,3,4,5-η)-1,5,6,7-tetrahydro-2-methyl-3-phenyl-s-indacen-1-yl]silanaminto(2-)-N]titanium (also referred to as dimethylsilyl(2-methyl-3-phenyl-s-indacenyl)(t-butylamido)Titaniumdimethyl

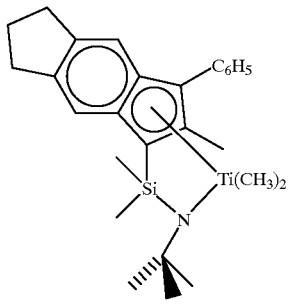

Preparation of dimethyl[N-(1,1-dimethylethyl)-1,1-dimethyl-[1,2,3,4,5-η)-1,5,6,7-tetrahydro-2-methyl-3-phenyl-s-indacen-1-yl]silanaminto(2-)-N]titanium Dichloro[N-(1,1-dimethylethyl)-1,1-dimethyl-[1,2,3,4,5-η)-1,5,6,7-tetrahydro-2-methyl-3-phenyl-s-indacen-1-yl]silanaminto(2-)-N]titanium (0.6774 g, 0.001376 moles) was stirred in diethylether (50 mL) as MeMgBr (0.002760 moles, 0.92 mL of 3.0 M solution in diethylether) was added slowly. This mixture was then stirred for 1 hour. After the reaction period the volatiles were removed and the residue extracted and filtered using hexane. Removal of the hexane resulted in the isolation of the desired product as a sticky yellow-red residue (0.4965 g, 79.9 percent).

Example 11

Synthesis of: dichloro[N-(cyclohexyl)-1,1-dimethyl-[1,2,3,4,5-η)-1,5,6,7-tetrahydro-2-methyl-3-phenyl-s-indacen-1-yl]silanaminto(2-)-N]titanium (also referred to as dimethylsilyl(2-methyl-3-phenyl-s-indacenyl)(cyclohexylamido)Titaniumdichloride

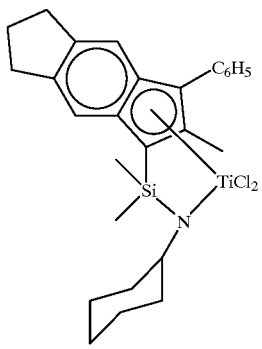

11a) Preparation of N-(cyclohexyl)-1,1-dimethyl-1-(1,5,6,7-tetrahydro-2-methyl-3-phenyl-s-indacen-1-yl)silanamine Chlorodimethyl(1,5,6,7-tetrahydro-2-methyl-3-phenyl-s-indacen-1-yl) silane (9c)) (5.5340 g, 0.01633 moles) was stirred in hexane (100 mL) as NEt$_3$ (2.9673 g, 0.02932 moles) and cyclohexylamine (1.6373 g, 0.01651 moles)

were added. This mixture was allowed to stir for 24 hours. After the reaction period the mixture was filtered and the volatiles removed resulting in the isolation of the desired product as a yellow oil (5.8969 g, 89.9 percent).

11b) Preparation of [N-(cyclohexyl)-1,1-dimethyl-[1,2,3,4,5-η)-1,5,6,7-tetrahydro-2-methyl-3-phenyl-s-indacen-1-yl]silanaminto(2-)-N]dilithium N-(cyclohexyl)-1,1-dimethyl-1-(1,5,6,7-tetrahydro-2-methyl-3-phenyl-s-indacen-1-yl)silanamine (5.8969 g, 0.01468 moles) was stirred in hexane (100 mL) as nBuLi (0.032 moles, 16.00 mL of 2.0 M solution in cyclohexane) was added slowly. This mixture was then allowed to stir 16 hours during which time a sticky precipitate formed. The volatiles were then removed and the resulting pale yellow solid slurried in cold hexane. After the reaction period the solid was collected via suction filtration as a yellow powder which was used without further purification or analysis (5.3101 g, 87.5 percent).

11c) Preparation of dichloro[N-(cyclohexyl)-1,1-dimethyl-[1,2,3,4,5-η)-1,5,6,7-tetrahydro-2-methyl-3-phenyl-s-indacen-1-yl]silanaminto(2-)-N]titanium

[N-(cyclohexyl)-1,1-dimethyl-[1,2,3,4,5-η)-1,5,6,7-tetrahydro-2-methyl-3-phenyl-s-indacen-1-yl]silanaminto(2-)-N]dilithium (5.3103 g, 0.01284 moles) in THF (50 mL) was added dropwise to a slurry of TiCl$_3$(THF)$_3$ (4.7570 g, 0.01284 moles) in THF 100 mL). This mixture was allowed to stir for 2 hours. PbCl$_2$ (1.8896 g, 0.006795 moles) was then added and the mixture allowed to stir for an additional hour. After the reaction period the volatiles were removed and the residue extracted and filtered using toluene. Removal of the toluene resulted in the isolation of a dark residue. This residue was then slurried in hexane and cooled to −10° C. The desired product was then isolated via filtration as a red crystalline solid (3.0765 g, 46.2 percent).

Example 12

Synthesis of: dimethyl[N-(cyclohexyl)-1,1-dimethyl-[1,2,3,4,5-η)-1,5,6,7-tetrahydro-2-methyl-3-phenyl-s-indacen-1-yl]silanaminto(2-)-N]titanium (also referred to as dimethylsilyl(2-methyl-3-phenyl-s-indacenyl)(cyclohexylamido) Titaniumdimethyl

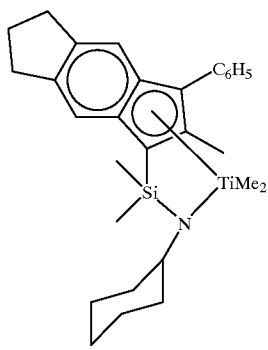

Dichloro[N-(cyclohexyl)-1,1-dimethyl-[1,2,3,4,5-η)-1,5,6,7-tetrahydro-2-methyl-3-phenyl-s-indacen-1-yl]silanaminto(2-)-N]titanium (0.7164 g, 0.001382 moles) was stirred in diethylether (50 mL) as MeMgBr (0.002760 moles, 0.92 mL of 3.0 M solution in diethylether) was added slowly. This mixture was then stirred for 1 hour. After the reaction period the volatiles were removed and the residue extracted and filtered using hexane. Removal of the hexane resulted in the isolation of the desired product as a sticky yellow-red residue (0.5102 g, 77.3 percent).

Example 13

Synthesis of: dichloro[N-(1,2-dimethylethyl)-1,1-dimethyl-[1,2,3,4,5-η)-1,5,6,7-tetrahydro-3-phenyl-s-indacen-1-yl]silanaminto(2-)-N]titanium (also referred to as dimethylsilyl(3-phenyl-s-indacen-1-yl)(t-butylamido)Titaniumdichloride

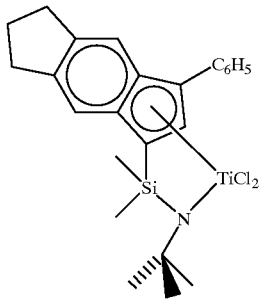

13a) Preparation of s-hydrindacen-1(2H)-one-3,5,6,7-tetrahydro

Indan (94.00 g, 0.7954 moles) and 3-chloropropionyl chloride (100.99 g, 0.7954 moles) were stirred in CH$_2$Cl$_2$ (300 mL) at 0° C. as AlCl$_3$ (130.00 g, 0.9750 moles) was added slowly under a nitrogen flow. The mixture was then allowed to stir at 20–25° C. for 2 hours. The volatiles were then removed. The mixture was then cooled to 0° C. and concentrated H$_2$SO$_4$ (500 mL) slowly added resulting in formation of a precipitate . The mixture was then left under nitrogen for 16 hours at 20–25° C. The mixture was then heated to 90° C. while stirring. After 2 hours crushed ice was added and the mixture agitated. The mixture was then transferred to a beaker and washed with H$_2$O and diethylether. The fractions were filtered and combined. The mixture was extracted with H$_2$O (2×200 mL). The organic layer was then separated and the volatiles removed. The desired product was then isolated via recrystallization from hexane at 0° C. as pale yellow crystals (22.36 g, 16.3 percent).

13b) Preparation of s-Indacen-1,2,3,5-tetrahydro-7-phenyl s-Hydrindacen-1(2H)-one-3,5,6,7-tetrahydro (12.00 g, 0.06967 moles) was stirred in diethylether (200 mL) at 0° C. as PhMgBr (0.105 moles, 35.00 mL of 3.0 M solution in diethylether) was added slowly. This mixture was then allowed to stir 16 hours at 20–25° C. After the reaction period the mixture was quenched by pouring over ice. The mixture was then acidified (pH=1) with HCl and stirred vigorously for 2 hours. The organic layer was then separated and washed with H$_2$O (2×100 mL) and then dried over MgSO$_4$. Filtration followed by the removal of the volatiles resulted in the isolation of the desired product as a dark oil (14.68 g, 90.3 percent).

13c) Preparation of (7-phenyl-1,2,3,5-tetrahydro-s-indacenyl)lithium s-Indacen-1,2,3,5-tetrahydro-7-phenyl (14.68 g, 0.06291 moles) was stirred in hexane (150 mL) as nBuLi (0.080 moles, 40.00 mL of 2.0 M solution in cyclohexane) was slowly added. This mixture was then allowed to stir 16 hours. After the reaction period the solid was collected via suction filtration as a yellow solid which was used without further purification or analysis (12.2075 g, 81.1 percent).

13d) Preparation of chlorodimethyl(1,5,6,7-tetrahydro-3-phenyl-s-indacen-1-yl)silane (7-phenyl-1,2,3,5-tetrahydro-s-indacenyl)lithium (12.2075 g, 0.05102 moles) in THF (50 mL) was added dropwise to a solution of $Me_2SiCl_2$ (19.5010 g, 0.1511 moles) in THF (100 mL) at 0° C. This mixture was then allowed to stir at 20–25° C. for 16 hours. After the reaction period the volatiles were removed and the residue extracted and filtered using hexane. The removal of the hexane resulted in the isolation of the desired product as a yellow oil (15.1492 g, 91.1 percent).

13e) Preparation of N-(1,1-dimethylethyl)-1,1-dimethyl-1-(1,5,6,7-tetrahydro-3-phenyl-s-indacen-1-yl)silanamine Chlorodimethyl(1,5,6,7-tetrahydro-3-phenyl-s-indacen-1-yl)silane (10.8277 g, 0.03322 moles) was stirred in hexane (150 mL) as $NEt_3$ (3.5123 g, 0.03471 moles) and t-butylamine (2.6074 g, 0.03565 moles) were added. This mixture was allowed to stir for 24 hours. After the reaction period the mixture was filtered and the volatiles removed resulting in the isolation of the desired product as a thick red-yellow oil (10.6551 g, 88.7 percent).

13f) Preparation of [N-(1,1-dimethylethyl)-1,1-dimethyl-[1,2,3,4,5-η)-1,5,6,7-tetrahydro-3-phenyl-s-indacen-1-yl]silanaminto(2-)-N]dilithium N-(1,1-dimethylethyl)-1,1-dimethyl-1-(1,5,6,7-tetrahydro-3-phenyl-s-indacen-1-yl)silaneamine (10.6551 g, 0.02947 moles) was stirred in hexane (100 mL) as nBuLi (0.070 moles, 35.00 mL of 2.0 M solution in cyclohexane) was added slowly. This mixture was then allowed to stir 16 hours during which time no salts crashed out of the dark red solution. After the reaction period the volatiles were removed and the residue quickly washed with hexane (2×50 mL). The dark red residue was then pumped dry and used without further purification or analysis (9.6517 g, 87.7 percent).

13g) Preparation of dichloro[N-(1,1-dimethylethyl)-1,1-dimethyl-1-[(1,2,3,4,5-η)-1,5,6,7-tetrahydro-3-phenyl-s-indacen-1-yl]silanaminato(2-)-N]titanium

[N-(1,1-dimethylethyl)-1,1-dimethyl-[1,2,3,4,5-η)-1,5,6,7-tetrahydro-3-phenyl-s-indacen-1-yl]silanaminto(2-)-N] dilithium (4.5355 g, 0.01214 moles) in THF (50 mL) was added dropwise to a slurry of $TiCl_3(THF)_3$ (4.5005 g, 0.01214 moles) in THF (100 mL). This mixture was allowed to stir for 2 hours. $PbCl_2$ (1.7136 g, 0.006162 moles) was then added and the mixture allowed to stir for an additional hour. After the reaction period the volatiles were removed and the residue extracted and filtered using toluene. Removal of the toluene resulted in the isolation of a dark residue. This residue was then slurried in hexane and cooled to 0° C. The desired product was then isolated via filtration as a red-brown crystalline solid (2.5280 g, 43.5 percent). FIG. 2 is the X-ray crystal structure of the complex.

Example 14

Synthesis of dimethyl[N-(1,1-dimethylethyl)-1,1-dimethyl-[1,2,3,4,5-η)-1,5,6,7-tetrahydro-3-phenyl-s-indacen-1-yl]silanaminto(2-)-N]titanium (also referred to as dimethylsilyl(3-phenyl-s-indacen-1-yl)(t-butylamido)Titaniumdimethyl

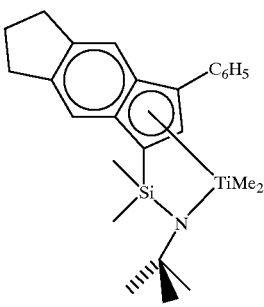

Dichloro[N-(1,1-dimethylethyl)-1,1-dimethyl-1-[(1,2,3,4,5-η)-1,5,6,7-tetrahydro-3-phenyl-s-indacen-1-yl] silanaminato(2-)-N]titanium (0.4970 g, 0.001039 moles) was stirred in diethylether (50 mL) as MeMgBr (0.0021 moles, 0.70 mL of 3.0 M solution in diethylether) was added slowly. This mixture was then stirred for 1 hour. After the reaction period the volatiles were removed and the residue extracted and filtered using hexane. Removal of the hexane resulted in the isolation of the desired product as a golden yellow solid (0.4546 g, 66.7 percent).

Example 15

Synthesis of dichloro[N-(cyclohexyl)-1,1-dimethyl-[1,2,3,4,5-η)-1,5,6,7-tetrahydro-3-phenyl-s-indacen-1-yl]silanaminto(2-)-N]titanium (also referred to as dimethylsilyl(3-phenyl-s-indacen-1-yl) (cyclohexylamido)Titaniumdichloride

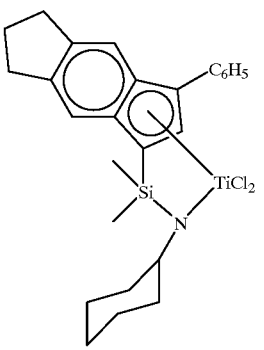

15a) Preparation of N-(cyclohexyl)-1,1-dimethyl-1-(1,5,6,7-tetrahydro-3-phenyl-s-indacen-1-yl) silanamine Chlorodimethyl(1,5,6,7-tetrahydro-3-phenyl-s-indacen-1-yl) silane (3.8523 g, 0.01182 moles) was stirred in hexane (100 mL) as $NEt_3$ (1.5136 g, 0.01496 moles) and cyclohexylamine (1.2107 g, 0.01221 moles) were added. This mixture was allowed to stir for 24 hours. After the reaction period the mixture was filtered and the volatiles removed resulting in the isolation of the desired product as a yellow oil (4.3313 g, 94.5 percent).

15b) Preparation of [N-(cyclohexyl)-1,1-dimethyl-[1,2,3,4,5-η)-1,5,6,7-tetrahydro-3-phenyl-s-indacen-1-yl]silanaminto(2-)-N]dilithium N-(cyclohexyl)-1,1-dimethyl-1-(1,5,6,7-tetrahydro-3-phenyl-s-indacen-1-yl)silanamine (4.3313 g, 0.01117 moles) was stirred in hexane (100 mL) as nBuLi (0.024 moles, 12.00 mL of 2.0 M solution in cyclohexane) was added slowly. This mixture was then allowed to stir 16 hours during which time a sticky precipitate formed. The volatiles were then removed and the resulting pale yellow solid slurried in cold hexane. After the reaction period the solid was collected via suction filtration as a red crystalline powder which was used without further purification or analysis (5.3101 g, 87.5 percent).

13c) Preparation of dichloro[N-(cyclohexyl)-1,1-dimethyl-1-[(1,2,3,4,5-η)-1,5,6,7-tetrahydro-3-phenyl-s-indacen-1-yl]silanaminato(2-)-N]titanium

[N-(cyclohexyl)-1,1-dimethyl-[1,2,3,4,5-η)-1,5,6,7-tetrahydro-3-phenyl-s-indacen-1-yl]silanaminto(2-)-N] dilithium (4.2135 g, 0.01055 moles) in THF (50 mL) was added dropwise to a slurry of TiCl$_3$(THF)$_3$ (3.9085 g, 0.01055 moles) in THF (100 mL). This mixture was allowed to stir for 2 hours. PbCl$_2$ (1.5373 g, 0.005529 moles) was then added and the mixture allowed to stir for an additional hour. After the reaction period the volatiles were removed and the residue extracted and filtered using toluene. Removal of the toluene resulted in the isolation of a dark residue. This residue was then slurried in hexane and cooled to 0° C. The desired product was then isolated via filtration as a red-brown crystalline solid (2.7655 g, 52.0 percent).

Example 16

Synthesis of dimethyl[-(cyclohexyl)-1,1-dimethyl-[(1,2,3,4,5-η)-1,5,6,7-tetrahydro-3-phenyl-s-indacen-1-yl]silanaminto(2-)-N]titanium (also referred to as dimethylsilyl(3-phenyl-s-indacen-1-yl)(cyclohexylamido)Titaniumdimethyl Dichloro[N-(cyclohexyl)-1,1-dimethyl-1-[(1,2,3,4,5-η)-1,5,6,7-tetrahydro-3-phenyl-s-indacen-1-yl]silanaminato(2-)-N]titanium (0.5581 g, 0.001106 moles) was stirred in diethylether (50 mL) as MeMgBr (0.0022 moles, 0.74 mL of 3.0 M solution in diethylether) was added slowly. This mixture was then stirred for 1 hour. After the reaction period the volatiles were removed and the residue extracted and filtered using hexane. Removal of the hexane resulted in the isolation of the desired product as a yellow-red residue (0.2118 g, 41.3 percent).

Example 17

Preparation of dichloro[N-(1,1-dimethylethyl)-1,1-dimethyl-(1,2,3,4,5-η))(5,6,7,8-tetrahydro-5,5,8,8-tetramethyl-3-phenyl-1H-Benz(f)inde-1-yl)silanaminato(2-)-N]titanium (also known as dimethylsilyl(n5-3-phenyl-s-5,5,8,8-tetramethylacenaphthalenyl-1-yl)(t-butylamido) Titaniumdichloride

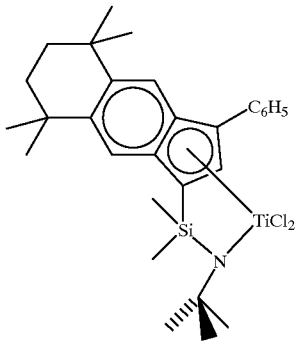

17a) Preparation of 2,3,5,7-tetrahydro-5,5,7,7-tetramethyl-1H-Benz(f)inden-1-one A solution of 5,6,7,8-tetrahydro-5,5,8,8-tetramethyl naphthalene (56 g, 0.29 mol) and 3-chloropropionyl chloride (37.5 g, 0.29 mol) in methylene chloride (50 ml) was added to a stirred solution of aluminum chloride (39.9 g, 0.3mol) in methylene chloride (200 ml). The mixture was stirred at 20–25° C. for 2 hr and poured into ice water. The methylene chloride layer was separated and dried over magnesium sulfate and the volatiles removed to yield as oil (80 g). The oil was added to a stirred solution of concentrated sulfuric acid (300ml) and heated to 70° C. for 5 hr and then to 80° C. for 5 hr. The reaction mixture was poured into water and extracted with methylene chloride (200 ml). The methylene chloride layer was dried over magnesium sulfate and the volatiles removed. The residue was slurried in hot hexane and filtered to yield the product as a yellow solid (yield 2 g, 3 percent).

17b) Preparation of 5,6,7,8-tetrahydro-5,6,7,8-tetramethyl-3-phenyl-1H-Benz(f)indene 2,3,5,7-tetrahydro-5,5,7,7-tetramethyl-1H-Benz(f)inden-1-one (1.74 g, 0.09 mol) was dissolved in tetrahydrofuran (50ml) and treated with a solution of phenyl magnesium bromide (10 ml of 1 M solution in THF) and allowed to stir for 1 hr at room temperature. The reaction mixture was poured into water and extracted with benzene. The benzene layer was separated and dried over magnesium sulfate. p-Toluene sulfonic acid (0.05 g) was added to the benzene solution and refluxed for 2 hr. The reaction mixture was contacted with 5 percent aqueous sodium bicarbonate solution. The benzene layer was separated, dried over anhydrous magnesium sulfate and the volatiles removed to yield the product as a oil (1.8 g, 62 percent).

17c) Preparation of N-(1,1-dimethylethyl)-1,1-dimethyl-1-(5,6,7,8-tetrahydro-5,5,8,8-tetramethyl-3-phenyl-1H-Benz(f)inde-1-yl)silanamine 5,6,7,8-Tetrahydro-5,5,8,8,-tetramethyl-3-phenyl-1H-Benz(f)indene (0.7270 g, 0.002404 moles) was stirred in hexane (50 mL) as nBuLi (0.0026 moles, 1.04 mL of 2.5 M solution on hexane) was added slowly. This mixture was allowed to stir for 6 hours. The volatiles were then removed and the residue redissolved in THF (30 mL) and added dropwise to a solution of dimethylsilyl(t-butylamino) chloride (0.4917 g, 0.002967 moles) in THF (50 mL). This mixture was then allowed to stir 16 hours. After the reaction period the volatiles were removed and the residue extracted and filtered using hexane. Removal of the hexane resulted in the isolation of the desired product as a pale yellow oil which was used without further purification or analysis (1.0037 g, 96.7 percent).

17d) Preparation of dichloro[N-(1,1-dimethylethyl)-1,1-dimethyl-(1,2,3,4,5-η1)(5,67.8-tetrahydro-5,5,8,8-tetramethyl-3-phenyl-1H-Benz(f)-1-yl)silanaminato(2-)-N]titanium N-(1,1-dimethylethyl)-1,1-dimethyl-1-(5,6,7,8-tetrahydro-5,5,8,8-tetramethyl-3-phenyl-1H-Benz(f)inde-1-yl)-silanamine (1.0037 g, 0.002325 moles) was stirred in hexane (50 mL) as n-BuLi (0.00475 moles, 1.90 mL of 2.5 M solution in hexane) was added. This mixture was then allowed to stir 16 hours. The volatiles were then removed from the mixture and the yellow residue dissolved in THF (25 mL) and added dropwise to a slurry of $TiCl_3(THF)_3$ (0.8616 g, 0.002325 moles). This mixture was allowed to stir for 2 hours. $PbCl_2$ (0.3678 g) was then added. After the reaction period the volatiles were removed and the residue extracted and filtered using toluene. Removal of the toluene resulted in the isolation of a dark residue. This residue was then redissolved in hexane and refiltered. Removal of the hexane resulted in the isolation of the desired product as a dark residue (0.7400 g, 55.0 percent).

Example 18

Preparation of dimethyl[N-(1,1-dimethylethyl)-1,1-dimethyl-(1,2,3,4,5-η)(5,6,7,8-tetrahydro-5,5,8,8-tetramethyl-3-phenyl-1H-Benz(f)inde-1-yl)silanaminato(2-)-N]titanium (also known as dimethylsilyl(n5-3-phenyl-s-5,5,8,8-tetramethylacenaphthalenyl-1-yl)(t-butylamido) Titaniumdimethyl

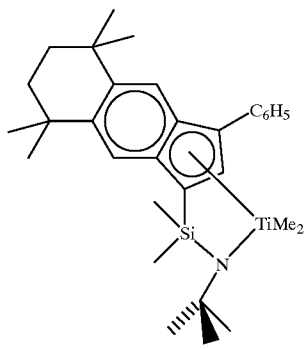

Dichloro[N-(1,1-dimethylethyl)-1,1-dimethyl-(1,2,3,4,5-η)(5,6,7,8-tetrahydro-5,5,8,8-tetramethyl-3-phenyl-1H-Benz(f)inde-1-yl)silanaminato(2-)-N]titanium (0.7400 g, 0.001349 moles) was stirred in diethylether (75 mL) as MeMgBr (0.0027 moles, 0.90 mL of 3.0 M solution in diethylether) was added slowly. This mixture was then allowed to stir for one hour. After the reaction period the volatiles were removed and the residue extracted and filtered using hexane. Removal of the hexane resulted in the isolation of the desired product as a dark solid (0.5568 g, 81.3 percent).

Example 19

Preparation of dichloro[N-(1,1-dimethylethyl)-1,1-dimethyl-(1,2,3,4,5-,n)(5,6,7,8-tetrahydro-2,5,5,8,8-pentamethyl-1H-Benz(f)inde-1-yl)silanaminato(2-)-N]titanium (also known as dimethylsilyl($\eta^5$-s-2,5,5,8,8-pentamethylacenaphthalenyl-1-yl)(t-butylamido) titanium dichloride

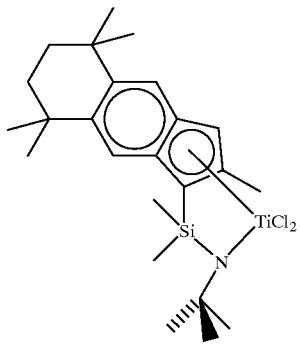

19a) Preparation of 1,1',4,4'-Tetramethyl-2,3-dihydronapthalene

Benzene (500 mL) and 2,3-dimethyl-2,3-butanediol (50.00 g, 341.9 mmol) were cooled in an ice-bath as solid $AlCl_3$ (100.30 g, 752.24 mmol) was slowly added over a 30 minute period of time under a nitrogen flow at 25° C. The mixture was stirred at 25° C for 30 minutes and then heated to 50° C. for 1 hour. Gas chromatography was used to monitor the completion of the reaction. After reaction completion the mixture was decanted over crushed ice leaving behind a small quantity of the denser oily phase. The decanted portion was transferred to an extraction funnel and washed with 1 M HCl (1×200 mL), saturated $NaHCO_3$ (2×200 mL), and $H_2O$ (1×200 mL). The organic fraction was then dried over $MgSO_4$. The mixture was then filtered and the volatiles removed from the filtrate resulting in the isolation of the desired product as a clear colorless oil (53.10 g, 82.5 percent yield).

$^1H$ NMR ($CDCl_3$): d 1.31 (s, 12H), 1.71 (s, 4H), 7.1–7.4 (m, 4H).

$^{13}C\{^1H\}$ NMR ($CDCl_3$): d 31.67, 34.19, 35.09, 125.50, 126.45, 144.76.

GC-MS Calculated for $C_{14}H_{20}$ 188.16, found 188.10.

19b) Preparation of 2,3,5,7-Tetrahydro-2,5,5,8,8-lentamethyl-1H-Benz(f)inden-1-one 1,1',4,4'-Tetramethyl-2,3-dihydronapthalene (30.00 g, 159.3 mmol) and 2-bromoisobutyryl bromide (36.62 g, 159.3 mmol) were stirred in $CH_2Cl_2$ (500 mL) at 0° C. as solid $AlCl_3$ (48.86 g, 366.4 mmol) was slowly added under a nitrogen flow over 30 minutes. This mixture was then allowed to stir for about 16 hours at about 20° C. After the reaction period the mixture was poured onto crushed ice. The organic layer was then separated and washed with 1 M HCl (1×200 mL), saturated $NaHCO_3$ (1×200 mL) and $H_2O$ (1×200 mL). The organic fraction was then dried over $MgSO_4$, filtered, and the volatiles removed resulting in the isolation of a dark crystalline residue. Recrystallization from diethylether (0° C.) resulted in the isolation of the $^1$H NMR (CDCl$_3$): d 1.2–1.4 (m, 15H), 1.71 (s, 4H), 2.6–2.7 (m, 2H), 3.34 (dd, $^2J_{H-H}$=17.6 Hz, $^3J_{H-H}$=8.7 Hz, 1H), 7.41 (s, 1H), 7.76 (s, 1H).

$^{13}$C{$^1$H} NMR (CDCl$_3$): d 16.50, 31.98, 32.09, 32.14, 34.58, 34.84, 35.25, 42.30, 121.92, 124.18, 133.85, 144.77, 149.94, 152.94, 209.05.

GC-MS Calculated for C$_{18}$H$_{24}$O 256.18, found 256.15.

19c) Preparation of 5,6,7.8-Tetrahydro-2,5,5,8,8-pentamethyl-1H-benz(f)indene (2,3,5,7-Tetrahydro-2,5,5,8,8-pentamethyl-1H-Benz(f) inden-1-one (14.89 g, 58.08 mmol) and NaBH$_4$ (2.21 g, 58.5 mmol) were stirred in diethylether (200 mL) at 0° C. as ethanol (100 mL) was added slowly. This mixture was allowed to warm slowly to room temperature and then stirred at room temperature overnight. After the reaction period the mixture was poured onto crushed ice and made acidic with HCl. The organic layer was then separated and washed with 1M HCl (1×100 mL). The volatiles were then removed from the organic layer and the residue refluxed in benzene (300 mL) with ptoluenesulfonic acid (0.12 g) using a Dean-Stark apparatus until no more H$_2$O was evolved. The mixture was then washed with 1 M NaHCO$_3$ (2×100 mL) and the volatiles were removed from the organic layer resulting in the isolation of a yellow oil. Recrystallization from MeOH (0° C.) gave the desired product as off-white crystals (10.37 g, 74.3 percent yield).

$^1$H NMR (CDCl$_3$): d 1.43 (s, 12H), 1.82 (s, 4H), 2.24 (s, 3H), 3.36 (s, 2H), 6.54 (s, 1H), 7.33 (s, 1H), 7.45 (s, 1H)

$^{13}$C{$^1$H} NMR (CDCl$_3$): d 16.94, 32.25, 34.44, 35.46, 42.44, 117.33, 121.21, 126.80, 139.89, 140.52, 142.55, 143.46, 145.20

GC-MS Calculated for C$_{18}$H$_{24}$ 240.19, found 240.15

19d) Preparation of 5,6,7.8-Tetrahydro-2,5,5,8,8-pentamethyl-1H-benz(f)indene, lithium salt 5,6,7,8-Tetrahydro-2,5,5,8,8-pentamethyl-1H-benz(f) indene (3.103 g, 12.91 mmol) was stirred in hexane (75 mL) as n-BuLi (12.91 mmol, 5.16 mL of 2.5 M solution in hexane) was added dropwise. This mixture was then allowed to stir for about 16 hours during which time a precipitate formed. The precipitate was collected via filtration, washed with hexane, and dried under vacuum. This product was used without further purification or analysis (2.087 g, 65.6 percent yield).

19e) Preparation of N-(1,1-Dimethylethyl)-5,6,7,8-tetrahydro-1,1-dimethyl-1-(2,5,5,8,8-pentamethyl-1H-benz(f)inden-1-yl)silanamine A solution of 5,6,7,8-tetrahydro-2,5,5,8,8-pentamethyl-1H-benz(f)indene, lithium salt (3.372 g, 13.69 mmol) in THF (25 mL) was added dropwise to a solution of N-(tert-butyl)-N-(1-chloro-1,1-dimethylsilyl)amine (3.403 g, 20.53 mmol) in THF (50 mL). This mixture was then allowed to stir for about 16 hours. Afterwards the volatiles were removed and the residue extracted and filtered using hexane. Removal of the hexane resulted in the isolation of the desired product as a yellow oil (5.049 g, 99.8 percent yield).

$^1$H NMR (C$_6$D$_6$): d –0.30 (s, 3H), 0.19 (s, 3H), 1.05 (s, 9H), 1.32 (s, 3H), 1.34 (s, 3H), 1.40 (s, 3H), 1.46 (s, 3H), 1.70 (m, 4H), 2.16 (s, 3H), 3.19 (s, 1H), 6.57 (s, 1H), 7.41 (s, 1H), 7.53 (s, 1H)

$^{13}$C{$^1$H} NMR (C$_6$D$_6$): δ –0.32, 1.45, 18.15, 32.53, 32.75, 33.77, 34.50, 34.60, 35.91, 49.44, 50.28, 117.60, 121.53, 126.06, 139.00, 141.47, 143.18, 143.61, 147.13

19f) Preparation of N-(1,1-dimethylethyl)-5,6,7,8-tetrahydro-1l1-dimethyl-1-(2,5,5,8,8-pentmethyl-1H-benz(f)inden-1-yl)silanamine, dilithium salt N-(1,1-Dimethylethyl)-5,6,7,8-tetrahydro-1,1-dimethyl-1-(2,5,5,8,8-pentamethyl-1H-benz(f)inden-1-yl)silanamine (5.049 g, 13.66 mmol) was stirred in hexane (75 mL) as n-BuLi (29.08 mmol, 14.54 mL of 2.0 M solution in cyclohexane) was added dropwise. After 2 hours this mixture was clear and yellow but had become extremely viscous. Diethylether (10 mL) was added to this mixture resulting in a decrease of the viscosity of the solution and the precipitation of a yellow solid. This mixture was allowed to stir overnight. After the reaction period the mixture was filtered resulting in the isolation of the desired product as a fine yellow powder which was washed with hexane, dried under vacuum, and used without further purification or analysis (4.135 g, 79.3 percent yield).

19g) Preparation of Dichloro(N-(1,1-dimethylethyl)-1,1-dimethyl-1-((1,2,3,3a,9a-η)-5,6,7,8-tetrahydro-2,5,5,8,8-pentamethyl-1H-benz(f)-1-yl)silanaminato(2-)-N)titanium N-(1,1-dimethylethyl)-5,6,7,8-tetrahydro-1,1-dimethyl-1-(2,5,5,8,8-pentamethyl-1H-benz(f)inden-1-yl)silanamine, dilithium salt (4.135 g, 10.84 mmol) in THF (25 mL) was added dropwise to a slurry of TiCl$_3$(THF)$_3$ (4.016 g, 10.84 mmol) in THF (75 mL). This mixture was allowed to stir for 1 hour. PbCl$_2$ (1.507 g, 5.420 mmol) was then added as a solid and the mixture allowed to stir for an additional hour. After the reaction period the volatiles were removed and the residue extracted and filtered using toluene. The toluene was then removed and the residue slurried in hexane and filtered. The solid was dried under vacuum resulting in the isolation of the desired product as a deep red microcrystalline solid (4.184 g, 79.0 percent yield).

$^1$H NMR (C$_6$D$_6$): d 0.47 (s, 3H), 0.71 (s, 3H), 1.21 (s, 3H), 1.25 (s, 3H), 1.28 (s, 3H), 1.33 (s, 3H), 1.36 (s, 3H), 1.56 (m, 4H), 2.21 (s, 3H), 6.78 (s, 1H), 7.46 (s, 1H), 7.78 (s, 1H)

$^{13}$C{$^1$H} NMR (C$_6$D$_6$): d 4.92, 5.35, 19.40, 32.35, 32.71, 32.97, 34.89, 35.04, 61.88, 149.76, 121.62, 123.39, 124.76, 133.43, 135.38, 144.75, 146.87, 148.74

HRMS (EI, M$^+$) Calculated for C$_{24}$H$_{37}$Cl$_2$NSiTi 485.15518, Found 485.1552

Example 20

Preparation of [N-(1,1-dimethylethyl)-1,1-dimethyl-(1,2,3,4,5-η)(5,6,7,8-tetrahydro-2,5,5,8,8-pentamethyl-1H-Benz(f)inde-1-yl)silanaminato(2-)-N]titanium dimethyl (also known as dimethylsilyl (η$^5$-s-2,5,5,8,8-pentamethylacenaphthalenyl-1-yl)(t-butylamido)titanium dimethyl)

MeMgBr (1.98 mmol, 0.66 mL of 3.0M solution in diethylether) was added dropwise to a solution of dichloro (N-(1,1-dimethylethyl)-1,1-dimethyl-1-((1,2,3,3a,9a-η)-5,6,7,8-tetrahydro-2,5,5,8,8-pentamethyl-1H-benz(f)inden-1-yl)silanaminato(2-)-N)titanium (0.439 g, 0.900 mmol) in diethylether (50 mL). This mixture was allowed to stir for 1 hour. After the reaction period the volatiles were removed and the residue extracted and filtered using hexane. Removal of the hexane resulted in the isolation of the desired product as a yellow oil (0.326 g, 81.2 percent yield).

Example 21

Preparation of 1,3-pentadiene [N-(1,1-dimethylethyl)-1,1-dimethyl-(1,2,3,4,5-η)(5,6,7,8-tetrahydro-2,5,5,8,8-pentamethyl-1H-Benz(f)inde-1-yl)silanaminato(2-)-N]titanium (also known as dimethylsilyl(η$^5$-s-2,5,5,8,8-pentamethylacenaphthalenyl-1-yl)(t-butylamido) titanium 1,3-pentadiene)

Dichloro(N-(1,1-dimethylethyl)-1,1-dimethyl-1-((1,2,3,3a,9a-η)-5,6,7,8-tetrahydro-2,5,5,8,8-pentamethyl-1H-Benz (f)inde-1-yl)silanaminato(2-)-N)titanium (0.600 g, 1.24 mmol) was dissolved in 50 ml of hexane. The reaction mixture was brought to gentle reflux. To this solution 0.62 ml (6.2 mmol) of piperylene was added at once followed by addition of n-BuMgCl (2.60 mmol, 1.3 mL of 2.0 M solution in diethylether). The mixture was refluxed for 1.5 hour. Upon cooling to room temperature the reaction mixture was filtered through a medium size frit, and solvent was removed under reduced pressure leaving 0.401 g of the desired product as a dark green viscous solid. Yield was 68 percent.

Example 22

Preparation of 2,4-hexadiene[N-(1,1-dimethylethyl)-1,1-dimethyl-[1,2,3,4,5-η)-1,5,6,7-tetrahydro-2-methyl-s-indacen-1-yl]silanaminato(2-)-N]titanium (also referred to as dimethylsilyl(2-methyl-s-indacenyl)(t-butylamido)titanium 2,4-hexadiene)

(t-Butylamido)dimethyl($\eta^5$-2-methyl-s-indacen-1-yl) silanetitanium dichloride (Example 1)) (0.300 grams, 0.72 mmol) is suspended in 50 mL of cyclohexane in a 100 mL round bottom flask. Ten equivalents of 2,4-hexadiene (0.822 mL, 7.21 mmol) are added to the contents of the flask followed by two and a quarter equivalents of a 2.0 M Et$_2$O solution of n-BuMgCl (0.81 mL, 1.62 mmol). The flask is fitted with a condenser and the reaction mixture is heated to reflux for one hour. Upon cooling, volatiles are removed under reduced pressure to leave a residue that is then extracted with hexane and filtered through a diatomaceous earth filter aid (Celite™) on a 10–15 mm glass frit. The hexane is removed under reduced pressure to afford 0.29 grams (g) of a brown oily solid as the desired product (equivalent to a 94 percent yield).

Example 23

Preparation of 1,3-pentadiene[N-(1,1-dimethylethyl)-1,1-dimethyl-[1,2,3,4,5-η)-1,5,6,7-tetrahydro-2-methyl-s-indacen-1-yl]silanaminto(2-)-N]titanium (also referred to as dimethylsilyl(2-methyl-s-indacenyl)(t-butylamido)titanium 1,3-pentadiene)

The reaction conditions of example 22 are substantially repeated excepting that 15 equivalents of 1,3-pentadiene (1.08 mL, 10.81 mmol) instead of the 10 equivalents of hexadiene and two equivalents of a 2.5 M hexane solution of n-BuLi (0.58 mL, 1.44 mmol) instead of the 2.25 equivalents of the 2.0 M Et$_2$O solution of n-BuMgCl is used. In addition, the reflux time is increased to three hours. As a result, 0.257 g of a brown oily solid (86 percent yield) of the desired product is obtained. The product is isolated as a mixture of the prone and supine isomers resulting from the orientation of 1,3-pentadiene.

Example 24

Synthesis of: 1,4-diphenyl-1,3-butadiene[N-(1,2-dimethylethyl)-1,1-dimethyl-[1,2,3,4,5-η)-1,5,6,7-tetrahydro-3-phenyl-s-indacen-1-yl]silanaminto(2-)-N]titanium (also referred to as dimethylsilyl(3-phenyl-s-indacen-1-yl)(t-butylamido)titanium 1,4-diphenyl-1,3-butadiene)

(t-Butylamido)dimethyl($\eta^5$-3-phenyl-s-indacen-1-yl) silanetitanium dichloride (Example 13) (0.478 grams, 1.00 mmol) is suspended in 40 mL of mixed hexanes in a 100 mL round bottom flask. One equivalent of 1,4-diphenyl-1,3-butadiene (0.206 g) is added to the contents of the flask followed by 2.1 equivalents of n-butyllithium (1.3 mL of a 1.60 M solution in hexanes). The flask is fitted with a condenser, stirred for 45 minutes at 20° C. and heated to reflux for 2.5 hours. Upon cooling, the mixture was filtered using a 0.45 μM pore size polytetrafluoroethylene filter. The volatiles are removed under reduced pressure to afford 0.606 g of product as a black oily solid, in 99 percent yield.

Example 25

Preparation of 1,3-pentadiene[N-(1,1-dimethylethyl)-1,1-dimethyl-(1,2,3,4,5-η)(5,6,7,8-tetrahydro-5,5,8,8-tetramethyl-3-phenyl-1H-Benz(f) inde-1yl)silanaminato(2-)-N]titanium (also known as dimethylsilyl($\eta^5$-3-phenyl-s-5,5,8,8-tetramethylacenaphthalenyl-1-yl)(t-butylamido) titanium 1,3-pentadiene)

(t-Butylamido)dimethyl($\eta^5$-3-phenyl-s-indacen-1-yl) silanetitanium dichloride (Example 13) (0.177 grams, 0.37 mmol) is suspended in 50 mL of mixed hexanes in a 100 mL round bottom flask. Fifteen molar equivalents of 1,3-pentadiene (0.55 mL) is added to the contents of the flask followed by 2.1 molar equivalents of n-butyllithium (0.5 mL of a 1.60 M solution in hexanes). The flask is fitted with a condenser and heated to reflux for 4 hours. Upon cooling, the mixture was filtered using diatomaceous earth filter aid and a glass frit filter. The volatiles are removed under reduced pressure to afford 0.197 g of an unpure, dark, olive green solid product along with what is believed to be low molecular weight poly-1,3-pentadiene, which was not readily seperable from the metal complex. The $^1$H NMR spectrum, indicated the presence of both the supine and and prone isomers of the metal complex.

Example 26

Synthesis of: 1,3-pentadiene[N-(1,2-dimethylethyl)-1,1-dimethyl-[1,2,3,4,5-η)-1,5,6,7-tetrahydro-3-phenyl-s-indacen-1-yl]silanaminto(2-)-N]titanium (also referred to as dimethylsilyl(3-phenyl-s-indacen-1-yl)(t-butylamido)titanium 1,3-pentadiene)

The conditions of Example 25 were substantially repeated using 0.9 g, (1.88 mmol) of (t-butylamido)dimethyl($\eta^5$-3-phenyl-s-indacen-1-yl)silanetitanium dichloride, one and one half molar equivalents of 1,3-pentadiene (0.3 mL), and 2.1 molar equivalents of n-butyllithium (2.5 mL of a 1.60 M solution in hexanes). The flask is again fitted with a condenser and heated to reflux for 4 hours. Upon cooling, the mixture was filtered using diatomaceous earth filter aid and a glass frit filter and the residue washed twice with 10 mL mixed hexanes. The volatiles were removed from the combined filtrates under reduced pressure to afford 0.777 g of the product as a dark, olive green solid containing 48 mole percent of the desired metal complex (85 weight percent yield). The product purity was higher than the product obtained in Example 25.

Polymerizations

Ethylene/Styrene Copolymerization

A two-liter Parr reactor is charged with approximately 360 g of Isopar-E™ mixed alkanes solvent (available from Exxon Chemicals Inc.) and about 460 g of styrene comonomer. Hydrogen is added as a molecular weight control agent by differential pressure expansion from a 75 mL addition tank at 25 psid (2070 kPa). The reactor is heated to 90° C. and saturated with ethylene at 200 psig (1.4 MPa). The appropriate amount of catalyst and cocatalyst (trispentafluorophenylborane) as 0.005 M solutions in toluene (approximately 2 µmole) are premixed in the drybox to give a 1:1 molar ratio of catalyst and cocatalyst. (Excepting for run 3 where the cocatalyst was methylalumoxane in a ratio Al:Ti of 1000:1.) After the desired premix time, the solution is transferred to a catalyst addition tank and injected into the reactor. The polymerization conditions are maintained for 30 minutes with ethylene on demand. Additional quantities of premixed catalyst are added periodically. The resulting solution is removed from the reactor, quenched with isopropyl alcohol and a hindered phenol antioxidant (Irganox™ 1010 from Ciba Geigy Corporation) is added to the resulting solution. Polymers formed are dried in a vacuum oven set at 135° C. for about 20 hours. Results using the catalysts of the invention are shown in Table 1.

TABLE 1

| Run | complex | Efficiency[1] | styrene[2] |
|---|---|---|---|
| 1 | Example 10 | 102 | 8.5 |
| 2 | Example 14 | 283 | 19.9 |
| 3* | Example 16 | 90 | 18.6 |

[1]kilograms polymer per gram Ti
[2]mole percent styrene
*MAO cocatalyst

Ethylene/1-Octene Copolymeriztion

A stirred 3.8 liter reactor was charged with 1440 g of Isopar-E™ mixed alkanes solvent (available from Exxon Chemicals Inc.) and 126 g of 1-octene comonomer. Hydrogen was added as a molecular weight control agent by differential pressure expansion from a 75 mL addition tank at 25 psid (2070 kPa). The reactor was heated to the polymerization temperature of 130° C. and saturated with ethylene at 450 psig (3.1 MPa). Approximately 2.0 µmol each of catalyst and trispentafluorophenylborane cocatalyst as 0.005 M solutions in toluene were premixed in a drybox, transferred to a catalyst addition tank and injected into the reactor over approximately a four minute period. The polymerization conditions were maintained for 10 minutes with ethylene on demand. The resulting solution was removed from the reactor, and a hindered phenol antioxidant (Irganox™ 1010 from Ciba Geigy Corporation) was added to the resulting solution. Polymers formed were dried in a vacuum oven set at 120° C. for about 20 hours. Results are contained in Table 2.

TABLE 2

| Run | complex | Efficiency[1] | MI[2] |
|---|---|---|---|
| 4 | Example 2 | 1,800 | 0.44 |
| 5 | Example 6 | 3,500 | 0.43 |
| 6 | Example 8 | 700 | 0.3 |

[1]kilograms polymer per gram Ti
[2]melt index $I_2$ dg/min

Ethylene/1-Octene Copolymerizations

A 2.0 liter Parr reactor is charged with approximately 740 g of Isopar-E™ mixed alkanes solvent (available from Exxon Chemicals Inc.) and 118 g of 1-octene comonomer. Hydrogen was added as a molecular weight control agent by differential pressure expansion from a 75 mL addition tank at 25 psid (2070 kPa). The reactor was heated to the polymerization temperature of 140° C. and saturated with ethylene at 500 psig. Then 0.5 µmol each of catalyst and $B(C_6F_5)_3$ cocatalyst as 0.005 M solutions in toluene were premixed in a drybox, transferred to a catalyst addition tank, and injected into the reactor. The polymerization conditions were maintained for 15 minutes with ethylene on demand. The resulting solution was removed from the reactor, and a hindered phenol antioxidant (67 mg of Irganox™ 1010+133 mg of Irgafos™ 168 from Ciba Geigy Corporation) was added to the resulting solution. Polymers formed were dried in a vacuum oven set at 140° C. for about 20 hours. Results are contained in Table 3

TABLE 3

| Run | Complex | Efficiency[2] | Density[3] | Melt Index (I2) |
|---|---|---|---|---|
| 7* | TCTP[1] | 2.0 | 0.902 | 6.4 |
| 8 | Ex. 2 | 1.5 | 0.889 | 0.43 |
| 9 | Ex. 25 | 1.5 | 0.889 | 0.10 |
| 10 | Ex. 26 | 1.1 | 0.891 | 0.095 |

*comparative, not an example of the invention
[1]TCTP = (t-butylamido)dimethyl(tetramethylcyclo-pentadienyl)titanium (II) 1,3-pentadiene
[2]Kg polymer/g Ti
[3]g/mL Continuous Solution Copolymerization Ethylene, propylene, and ethylidene norbornene (EPDM) terpolymer compositions are prepared using in a 23 L stirred, oil jacketed, autoclave reactor designed for continuous addition of reactants and continuous removal of polymer solution, devolatilization and polymer recovery, operating at 475 psig (3.3 MPa) pressure and 90° C. temperature. In Runs 11 and 12 the metal complex used was prepared according to Example 1. In Run 14 the metal complex used was a comparative complex, (t-butylamido)dimethyl (tetramethylcyclopentadienyl)silanetitanium 1,3-pentadiene. Ethylene flows for all polymerizations was 1.1 kg/h. Propylene flows for all polymerizations was 1.6 kg/h. Hydrogen, added as a molecular weight control agent was added at a flow rate of 26 scc/min. The cocatalyst for all polymerizations was a combination of trispentafluorophenyl-borane (FAB) and modified methylalumoxane (MMAO available from Akzo Nobel). In the process, ethylene, propylene, and hydrogen were combined into a single stream before being introduced into a diluent mixture comprising a mixed alkane solvent (Isopar-E™, available from Exxon Chemicals Inc.) and ethylidene norbornene (ENB) to form a combined feed mixture that was continuously injected into the reactor. The metal complex and the cocatalyst mixture were similarly combined in the same diluent and also continuously injected into the reactor.

The reactor exit stream was continuously removed from the reactor, injected with catalyst kill (water) and hindered bisphenol antioxidant, and introduced into a separator, where molten polymer was continuously separated from the unreacted monomers, hydrogen, and diluent. The molten polymer was fed to an extruder, formed into strands, cooled, pelletized and collected for analysis. Details of processing conditions and polymer properties are contained in Table 4.

TABLE 4

| Run | Diluent Flow (kg/h) | ENB Flow (kg/h) | Cat Flow (g/h) | FAB Flow (g/h) | MAO Flow (g/h) | $C_2$ Conv % | Prod. rate (kg/h) | Wt. % $C_3$ | Wt % ENB | Efficiency[1] | Polymer Mooney Viscosity[2] |
|---|---|---|---|---|---|---|---|---|---|---|---|
| 11 | 17.0 | 0.3 | 69 | 78 | 68 | 75.1 | 1.8 | 48 | 7.7 | 2.2 | 30 |
| 12 | 17.3 | 0.3 | 42 | 48 | 40 | 76.7 | 1.9 | 52 | 4.5 | 3.6 | 25 |
| 13 | 17.3 | 0.2 | 120 | 80 | 90 | 75.5 | 1.8 | 50 | 5.1 | 1.9 | 60 |
| 14* | 15.9 | 0.2 | 340 | 430 | 550 | 77.0 | 2.0 | 52 | 5.1 | 0.9 | 2 |

*not an example of the invention
[1] Kg polymer/g Ti
[2] ($ML_{1+4}$ @ 125° C., ASTM D1646-94)

The resulting polymers not only have significantly increased Mooney viscosity compared to the control, thereby indicating increased molecular weight, especially for run 13 using a titanium catalyst wherein the metal is in the +2 formal oxidation state, but the catalyst and cocatalyst efficiencies for the catalysts of the invention in preparing such polymers under essentially equivalent process rates and conditions were significantly improved.

What is claimed is:

1. A metal complex corresponding to the formula (I):

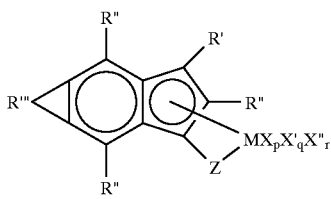

(I)

where M is titanium, zirconium or hafnium in the +2, +3 or +4 formal oxidation state;

R' and R" are independently each occurrence hydride, hydrocarbyl, silyl, germyl, halide, hydrocarbyloxy, hydrocarbylsiloxy, hydrocarbylsilylamino, di(hydrocarbyl)amino, hydrocarbyleneamino, di(hydrocarbyl)phosphino, hydrocarbylene-phosphino, hydrocarbylsulfido, halo-substituted hydrocarbyl, hydrocarbyloxy-substituted hydrocarbyl, silyl-substituted hydrocarbyl, hydrocarbylsiloxy-substituted hydrocarbyl, hydrocarbylsilylamino-substituted hydrocarbyl, di(hydrocarbyl)amino-substituted hydrocarbyl, hydrocarbyleneamino-substituted hydrocarbyl, di(hydrocarbyl)phosphino-substituted hydrocarbyl, hydrocarbylene-phosphino-substituted hydrocarbyl, or hydrocarbylsulfido-substituted hydrocarbyl, said R' or R" group having up to 40 nonhydrogen atoms, and optionally two or more of the foregoing groups may together form a divalent derivative;

R'" is a divalent hydrocarbylene- or substituted hydrocarbylene group forming a fused system with the remainder of the metal complex, said R'" containing from 1 to 30 nonhydrogen atoms;

Z is a divalent moiety, or a moiety comprising one (σ-bond and a neutral two electron pair able to form a coordinate-covalent bond to M, said Z comprising boron, or a member of Group 14 of the Periodic Table of the Elements, and also comprising nitrogen, phosphorus, sulfur or oxygen;

X is a monovalent anionic ligand group having up to 60 atoms exclusive of the class of ligands that are cyclic, delocalized, π-bound ligand groups;

X' independently each occurrence is a neutral ligating compound having up to 20 atoms;

X" is a divalent anionic ligand group having up to 60 atoms;

p is zero, 1, 2, or 3;

q is zero, 1 or 2, and r is zero or 1.

2. The metal complex of claim 1 wherein R'" corresponds to the formula:

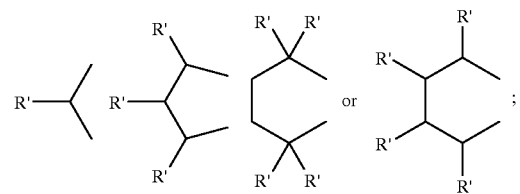

wherein R' is as previously defined in claim 1.

3. The metal complex of claim 1 corresponding to the formula:

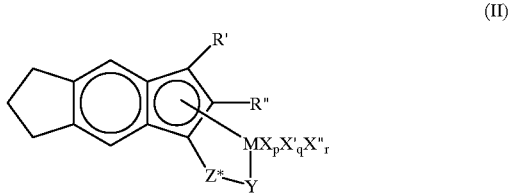

(II)

or

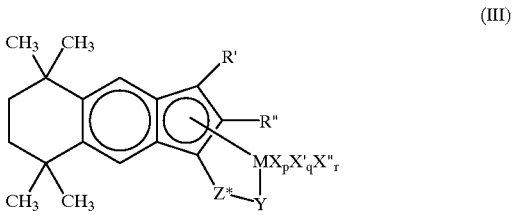

(III)

wherein:

R' is hydrocarbyl, di(hydrocarbylamino), or a hydrocarbyleneamino group, said R' having up to 20 carbon atoms, R" is $C_{1-20}$ hydrocarbyl or hydrogen;

is M is titanium;

Y is —O—, —S—, —NR*—, —PR*—;

Z* is $SiR*_2$, $CR*_2$, $SiR*_2SiR*_2$, $CR*_2CR*_2$, CR*=CR*, $CR*_2SiR*_2$, or $GeR*_2$;

R* each occurrence is independently hydrogen, or a member selected from hydrocarbyl, hydrocarbyloxy, silyl, halogenated alkyl, halogenated aryl, and combinations thereof, said R* having up to 20 non-hydrogen atoms, and optionally, two R* groups from Z (when R* is not hydrogen), or an R* group from Z and an R* group from Y form a ring system;

X, X', and X" are as defined in claim 1;

p is 0, 1 or 2;

q is zero or one; and r is zero or 1;

with the proviso that:
- when p is 2, q and r are zero, M is in the +4 formal oxidation state (or M is in the +3 formal oxidation state if Y is —NR*₂ or —PR*₂), and X is an anionic ligand selected from the group consisting of halide, hydrocarbyl, hydrocarbyloxy, di(hydrocarbyl)amido, di(hydrocarbyl)phosphido, hydrocarbylsulfido, and silyl groups, as well as halo-, di(hydrocarbyl)amino-, hydrocarbyloxy-, and di(hydrocarbyl)phosphino-substituted derivatives thereof, said X group having up to 30 nonhydrogen atoms,
- when r is 1, p and q are zero, M is in the +4 formal oxidation state, and X" is a dianionic ligand selected from the group consisting of hydrocarbadiyl, oxyhydrocarbyl, and hydrocarbylenedioxy groups, said X group having up to 30 nonhydrogen atoms,
- when p is 1, q and r are zero, M is in the +3 formal oxidation state, and X is a stabilizing anionic ligand group selected from the group consisting of allyl, 2-(N,N-dimethylamino)phenyl, 2-(N,N-dimethylaminomethyl)phenyl, and 2-(N,N-dimethylamino)benzyl, and
- when p and r are zero, q is 1, M is in the +2 formal oxidation state, and X' is a neutral, conjugated or nonconjugated diene, optionally substituted with one or more hydrocarbyl groups, said X' having up to 40 carbon atoms and forming π-complex with M.

4. A metal complex according to claim 1 corresponding to the formula:

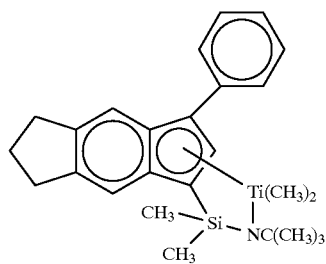

(IV)

or

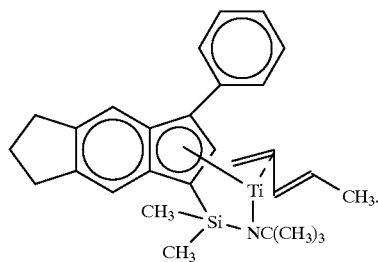

(V)

5. A metal complex according to claim 1 corresponding to the formula:

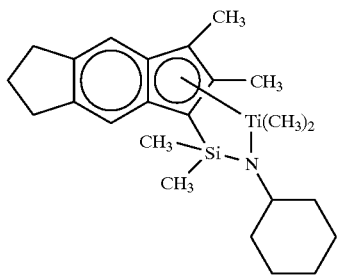

(VI)

or

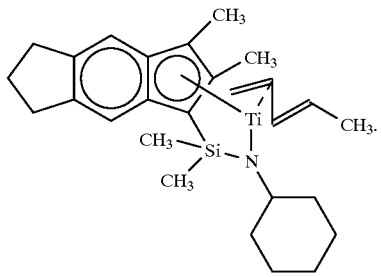

(VII)

6. A metal complex according to claim 1 corresponding to the formula:

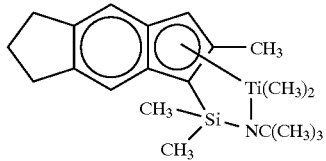

(VIII)

or

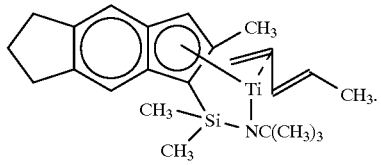

(IX)

7. A process for preparing a neutral diene complex corresponding to the formula:

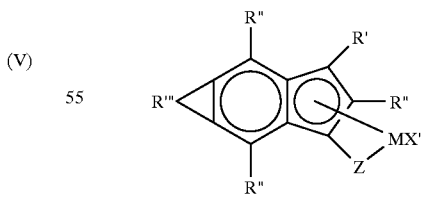

where M is titanium in the +2 formal oxidation state;

R' and R" are independently each occurrence hydride, hydrocarbyl, silyl, germyl halide, hydrocarbyloxy, hydrocarbylsiloxy, hydrocarbylsilylamino, di(hydrocarbyl)amino, hydrocarbyleneamino, di(hydrocarbyl)phosphino, hydrocarbylene-phosphino, hydrocarbylsulfido, halo-substituted hydrocarbyl, hydrocarbyloxy-substituted hydrocarbyl, silyl-substituted hydrocarbyl, hydrocarbylsiloxy-substituted hydrocarbyl, hydrocarbylsilylamino-substituted hydrocarbyl, di(hydrocarbyl)amino-substituted hydrocarbyl, hydrocarbyleneamino-substituted hydrocarbyl, di(hydrocarbyl)phosphino-substituted hydrocarbyl, hydrocarbylene-phosphino-substituted hydrocarbyl, or hydrocarbylsulfido-substituted hydrocarbyl, said R' or R" group having up to 40 nonhydrogen atoms, and optionally two or more of the foregoing groups may together form a divalent derivative;

R''' is a divalent hydrocarbylene- or substituted hydrocarbylene group forming a fused system with the remainder of the metal complex, said R''' containing from 1 to 30 nonhydrogen atoms;

Z is a divalent moiety, or a moiety comprising one σ-bond and a neutral two electron pair able to form a coordinate-covalent bond to M, said Z comprising boron, or a member of Group 14 of the Periodic Table of the Elements, and also comprising nitrogen, phosphorus, sulfur or oxygen; and X' independently is a neutral conjugated diene compound having up to 20 carbon atoms;

comprising contacting a metal complex corresponding to the formula:

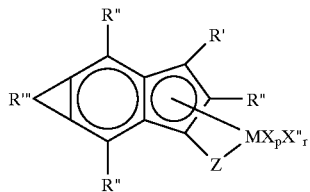

where M is titanium in the +3 or +4 formal oxidation state;

R', R", R''', and Z are as previously defined;

X is a monovalent anionic ligand group having up to 60 atoms exclusive of the class of ligands that are cyclic, delocalized, π-bound ligand groups;

X" is a divalent anionic ligand group having up to 60 atoms;

p is 1 or 2; and r is zero or 1 with from 1 to 2 equivalents of a neutral conjugated diene of the formula X' in an inert diluent i the presence of a reducing agent and recovering the resulting product.

8. The process of claim 7 wherein a reaction mixture comprising the metal complex and reducing agent is heated To a temperature from 50 to 95° C. prior to adding the conjugated diene.

* * * * *

UNITED STATES PATENT AND TRADEMARK OFFICE
CERTIFICATE OF CORRECTION

PATENT NO : 5,965,756

DATED : October 12, 1999

INVENTOR(S) : McAdon, et al.

It is certified that error appears in the above-identified patent and that said Letters Patent is hereby corrected as shown below:

On title page,

Item [75], Inventors should correctly read as follows — Mark H. McAdon; Jasson T. Patton; Peter N. Nickias; Ravi B. Shankar; Francis J. Timmers; Jerzy Klosin, all of Midland Mich., Daniel D. VanderLende, Sugar Land, Tex. — .

Signed and Sealed this

Thirteenth Day of June, 2000

*Attest:*

Q. TODD DICKINSON

*Attesting Officer*     *Director of Patents and Trademarks*